United States Patent
DiSanto

(10) Patent No.: US 6,455,060 B2
(45) Date of Patent: Sep. 24, 2002

(54) S(+) DESMETHYLSELEGILINE AND ITS USE TO TREAT IMMUNE SYSTEM DYSFUNCTION

(75) Inventor: Anthony R. DiSanto, Dade City, FL (US)

(73) Assignee: Somerset Pharmaceuticals, Inc., Tampa, FL (US)

(*) Notice: Subject to any disclaimer, the term of this patent is extended or adjusted under 35 U.S.C. 154(b) by 0 days.

(21) Appl. No.: 09/800,022

(22) Filed: Mar. 5, 2001

Related U.S. Application Data

(60) Division of application No. 09/448,483, filed on Nov. 24, 1999, now Pat. No. 6,210,706, which is a division of application No. 08/679,328, filed on Jul. 12, 1996, now Pat. No. 6,033,682, which is a continuation-in-part of application No. PCT/US96/01561, filed on Jan. 11, 1996, and a continuation-in-part of application No. 08/372,139, filed on Jan. 13, 1995, now abandoned.

(60) Provisional application No. 60/001,979, filed on Jul. 31, 1995.

(51) Int. Cl.$^7$ ............................................. A01N 43/36
(52) U.S. Cl. ........................ 424/422; 424/400; 424/428; 424/430; 424/449; 514/885; 514/889; 514/654
(58) Field of Search ...................... 514/654, 885, 514/889; 424/400, 449, 422, 430

(56) References Cited

U.S. PATENT DOCUMENTS

| | | | |
|---|---|---|---|
| 4,564,706 A | 1/1986 | Ecsery et al. ............... | 564/376 |
| 4,812,481 A | 3/1989 | Reischig et al. ............ | 514/647 |
| 4,861,800 A | 8/1989 | Buyske ........................ | 514/646 |
| 4,925,878 A | 5/1990 | Bodó et al. .................. | 514/646 |
| 5,075,338 A | 12/1991 | Knoll et al. ................. | 514/654 |
| 5,128,145 A | 7/1992 | Edgren et al. .............. | 424/473 |
| 5,190,763 A | 3/1993 | Edgren et al. .............. | 424/473 |
| 5,225,446 A | 7/1993 | Milgram ..................... | 514/654 |
| 5,234,957 A | 8/1993 | Mantelle ................... | 514/772.6 |
| 5,242,950 A | 9/1993 | Fries Hastings ............ | 514/654 |
| 5,276,057 A | 1/1994 | Milgram et al. ............ | 514/646 |
| RE34,579 E | 4/1994 | Buyske et al. .............. | 514/646 |
| 5,380,761 A | 1/1995 | Szabó et al. ................ | 514/655 |
| 5,387,615 A | 2/1995 | Milgram et al. ............ | 514/654 |

FOREIGN PATENT DOCUMENTS

| | | | |
|---|---|---|---|
| EP | 0 404 807 | 1/1991 | ......... A61K/31/135 |
| EP | 0 509 761 | 10/1992 | ......... A61K/31/135 |
| EP | 0 583 807 | 4/1994 | ............ A61K/9/70 |
| WO | WO 92/17169 | 10/1992 | ......... A61K/31/135 |

OTHER PUBLICATIONS

Life Extension Report, "Deprenyl Extends the Lifespan of Immunosuppressed Mice," 15(1):1–4, 1995.

Amenta et al., "Microanatomical Changes in the Frontal Cortex of Aged Rats: Effect of L–Deprenyl Treatment," *Brain Res. Bull.* 34:125–131 (1994).

(List continued on next page.)

Primary Examiner—Thurman K. Page
Assistant Examiner—Lakshmi Channavajjala
(74) Attorney, Agent, or Firm—Vinson & Elkins, L.L.P.

(57) ABSTRACT

The present invention provides novel compositions and methods for using the S(+) enantiomer of desmethylselegiline (N-methyl-N-(prop-2-ynyl)-2-aminophenylpropane), for the treatment of selegiline-responsive diseases and conditions. Diseases and conditions responsive to selegiline include those produced by neuronal degeneration or neuronal trauma and those due to immune system dysfunction. Effective dosages are a daily dose of at least about 0.015 mg/kg of body weight.

29 Claims, 17 Drawing Sheets

OTHER PUBLICATIONS

Ansari et al., "Rescue of Axotomized Immature Rat Facial Motoneurons by R(–)–Deprenyl: Stereospecificity and Independence from Monoamine Oxidase Inhibition," *J. Neurosci.* 13(9):4042–4053 (1993).

Berry et al., "Possible Mechanisms of Action of (–)Deprenyl and Other MAO–B Inhibitors in Some Neurologic and Psychiatric Disorders," *Prog. in Neurobiol.* 44:141–161 (1994).

Casper et al., "EFG Enhances the Survival of Dopamine Neurons in Rat Embryonic Mesencephalon Primary Cell Culture," *J. Neurosci. Res.* 30:372–381 (1991).

Glover et al., "Neurotoxins and Monoamine Oxidase B Inhibitors: Possible Mechanisms for the Neuroprotective Efffect of (–)–Deprenyl," *Inhibitors of Monoamine Oxidase B*, Chapter 8 (1993).

Iwasaki et al., "Deprenyl Enhances Neurite Outgrowth in Cultured Rat Spinal Ventral Horn Neurons," *J. Neurol Sci.* 125:11–13 (1994).

Ju et al., "(–)–Deprenyl Alters the Time Course of Death of Axotomized Facial Motoneurons and the Hypertrophy of Neighoring Astrocytes in Immature Rats," *Exp. Neurol.* 126:233–246 (1994).

Matsui et al., "Monoamine Oxidase Inhibitors Prevent Striatal Neuronal Necrosis Induced by Transient Forebrain Ischemia," *Neurosci. Lett.* 126:175–178 (1991).

Park et al., "Protection from 1–Methyl–4–Phenylpyridinium (MPP$^+$) Toxicity and Stimulation of Regrowth of MPP$^+$–damaged Dopaminergic Fibers by Treatment of Mesencephalic Cultures with EGF and Basic FGF," *Brain Res.* 599:83–97 (1992).

Rinne, "Nigral Degeneration in Parkinson's Disease in Relation to Clinical Features," *Acta Neurol. Scand.* 84(supp. 136):87–90 (1991).

Rinne et al., "Selegiline (Deprenyl) Treatment and Death of Nigral Neurons in Parkinson's Disease," *Neurology* 41:859–861 (1991).

Salo et al., "Deprenyl Reduces the Death of Motoneurons Caused by Axotomy," *J. Neurosci. Res.* 31:394–400 (1992).

Tatton, "Selegiline Can Mediate Neuronal Rescue Rather Than Neuronal Protection," *Movement Disorders* 8:520–530 (1993).

Tatton et al., "Trophic–Like' Actions of (–)–Deprenyl on Neurons and Astroglia," *in Recent Advances in the Treatment of Neurodegenerative Disorders and Cognitive Dysfunction* 7:238–248 (1994).

Zeng et al., "Influence of Long–Term Treatment with L–Deprenyl on the Age–Dependent Changes in Rat Brain Microanatomy," *Mech. Ageing Dev.* 73:113–126 (1994).

Borbe et al., "Kinetic Evaluation of MAO–B–Activity Following Oral Administration of Selegiline and Desmethyl–Selegiline in the Rat," *J. Neural. Transm.* 32:131–137 (19990).

Gershon et al., "Monoamide Oxidase Inhibition and the Induction of Ponto–Geniculo–Occipital Wave Activity by Reserpine in the Cat," *J. Pharmacol. Exp. Ther.* 197:556–566 (1976).

Heinonen et al., "Desmethylselegiline, a Metabolite of Selegiline, Is an Irreversible Inhibitor of MAO–B in Human Subjects," *Neurology* 43:A156 (1993).

Heinonen et al., "Pharmacokinetic Aspects of l–Deprenyl (Selegiline) and Its Metabolites," *Clin. Pharmacol. Ther.* 56:742–749 (1994).

Heinonen et al., "Pharmacokinetics and Metabolism of Selegiline," *Acta Neurol. Scand.* 126:93–99 (1989).

Martin et al., "Regression Analysis of the Relationship between Physical Properties and the in Vitro Inhibition of Monoamine Oxidase by Propynylamines," *J. Med. Chem.* 18:883–888 (1975).

Nickel et al., "Effect of Selegiline and Desmethyl–Selegiline on Cortical Electric Activity in Rats," *J. Neural. Transm.* 32:139–144 (1990).

Williams et al., "Biochemical and Behavioural Studies of Monoamine Oxidase Inhibition," *Ir. J. Med. Sci.* 147:71–74 (1978).

S(+) DESMETHYLSELEGILINE AND ITS USE TO TREAT IMMUNE SYSTEM DYSFUNCTION

CROSS REFERENCE TO RELATED APPLICATIONS

The present application is a division of U.S. application Ser. No. 09/448,483, filed on Nov. 24, 1999, which issued as U.S. Pat. No. 6,210,706. U.S. application Ser. No. 09/448,483 is a division of U.S. application Ser. No. 08/679,328, filed on Jul. 12, 1996, issued as U.S. Pat. No. 6,033,682, which was a continuation-in-part of PCT/US96/01561, with an international filing date of Jan. 11, 1996, a continuation-in-part of U.S. Ser. No. 60/011,979, filed Jul. 31, 1995, and a continuation-in-part of U.S. Ser. No. 08/372,139, filed Jan. 13, 1995 now abandoned.

FIELD OF THE INVENTION

The present invention provides a novel S(+) isomer of desmethylselegiline, i.e., a compound of the formula:

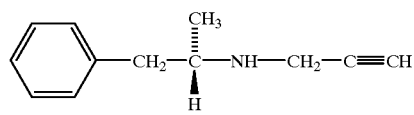

and further provides novel pharmaceutical and other compositions containing this isomer. In addition, the present invention provides novel methods for using this enantiomer in the treatment of selegiline-responsive diseases and conditions in animals, including humans.

BACKGROUND OF THE INVENTION

Two distinct monoamine oxidase enzymes are known in the art: monoamine oxidase A (MAO-A) and monoamine oxidase B (MAO-B). The cDNAs encoding these enzymes show different promoter regions and distinct exon portions, indicating they are encoded independently at different gene positions. In addition, analysis of the two proteins has shown differences in their respective amino acid sequences.

The first compound found to selectively inhibit MAO-B was R-(−)-N-methyl-N-(prop-2-ynyl)-2-aminophenylpropane, also known as L-(−)-deprenyl, R-(−)-deprenyl, or selegiline. Selegiline has the following structural formula:

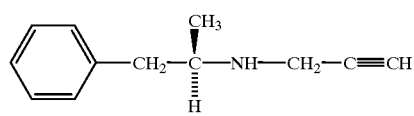

The selectivity of selegiline in the inhibition of MAO-B is important to its safety profile following oral administration. Inhibition of MAO-A may cause toxic side effects by interfering with the metabolism of tyramine. Tyramine is normally metabolized in the gastrointestinal tract by MAO-A but when MAO-A is inhibited, tyramine absorption is increased following consumption of tyramine-containing foods such as cheese, beer, herring, etc. This results in the release of catecholamines which can precipitate a hypertensive crisis, producing the "cheese effect." This effect is characterized by Goodman and Gilman as the most serious toxic effect associated with MAO-A inhibitors.

One of the metabolites of selegiline is its N-desmethyl analog. Structurally, desmethylselegiline is the R(−) enantiomeric form of a secondary amine of the formula:

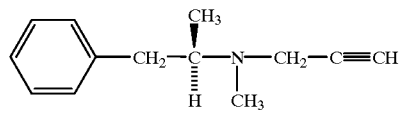

Heretofore, desmethylselegiline was not known to have pharmaceutically useful MAO-related effects, i.e., potent and selective inhibitory effects on MAO-B. In the course of determining the usefulness of desmethylselegiline for the purposes of the present invention, the MAO-related effects of desmethylselegiline were more completely characterized. This characterization has established that desmethylselegiline has exceedingly weak MAO-B inhibitory effects and no advantages in selectivity with respect to MAO-B compared to selegiline.

For example, the present characterization established that selegiline has an $IC_{50}$ value against MAO-B in human platelets of $5 \times 10^{-9}$ M whereas R(−)desmethylselegiline's $IC_{50}$ value is $4 \times 10^{-7}$ M, indicating the latter is approximately 80 times less potent as an MAO-B inhibitor than the former. Similar characteristics can be seen in the following data measuring inhibition of MAO-B and MAO-A in rat cortex mitochondrial-rich fractions:

TABLE 1

Inhibition of MAO by Selegiline and Desmethylselegiline

| | Percent Inhibition | | | |
|---|---|---|---|---|
| | selegiline | | R(−)desmethylselegiline | |
| Conc. | MAO-B | MAO-A | MAO-B | MAO-A |
| 0.003 μM | 16.70 | — | 3.40 | — |
| 0.010 μM | 40.20 | — | 7.50 | — |
| 0.030 μM | 64.70 | — | 4.60 | — |
| 0.100 μM | 91.80 | — | 6.70 | — |
| 0.300 μM | 94.55 | 9.75 | 26.15 | 0.0 |
| 1.000 μM | 95.65 | 32.55 | 54.73 | 0.70 |
| 3.000 μM | 98.10 | 65.50 | 86.27 | 4.10 |
| 10.000 μM | — | 97.75 | 95.15 | 11.75 |
| 30.000 μM | — | — | 97.05 | — |
| 100.000 μM | — | — | — | 56.10 |

As is apparent from the above table, selegiline is approximately 128 times more potent as an inhibitor of MAO-B relative to MAO-A, whereas desmethylselegiline is about 97 times more potent as an inhibitor of MAO-B relative to MAO-A. Accordingly, desmethylselegiline appears to have an approximately equal selectivity for MAO-B compared to MAO-A as selegiline, albeit with a substantially reduced potency.

Analogous results are obtained in rat brain tissue. Selegiline exhibits an $IC_{50}$ for MAO-B of $0.11 \times 10^{-7}$ M whereas desmethylselegiline's $IC_{50}$ value is $7.3 \times 10^{-7}$ M, indicating desmethylselegiline is approximately 70 times less potent as an MAO-B inhibitor than selegiline. Both compounds exhibit low potency in inhibiting MAO-A in rat brain tissue, $0.18 \times 10^{-5}$ for selegiline, $7.0 \times 10^{-5}$ for desmethylselegiline. Thus, in vitro R(−)desmethylselegiline is approximately 39 times less potent than selegiline in inhibiting MAO-A.

Based on its pharmacological profile as set forth above, R(−)desmethylselegiline as an MAO-B inhibitor provides no advantages in either potency or selectivity compared to selegiline. To the contrary, the above in vitro data suggest that use of desmethylselegiline as an MAO-B inhibitor requires on the order of 70 times the amount of selegiline.

The potency of desmethylselegiline as an MAO-B inhibitor in vivo has been reported by Heinonen, E: H., et al. ("Desmethylselegiline, a metabolite of selegiline, is an irreversible inhibitor of MAO-B in human subjects," referenced in Academic Dissertation "Selegiline in the Treatment of Parkinson's Disease," from Research Reports from the Department of Neurology, University of Turku, Turku, Finland, No. 33 (1995), pp. 59–61). According to Heinonen, desmethylselegiline in vivo has only about one-fifth the MAO-B inhibitory effect as selegiline, i.e., a dose of 10 mg of desmethylselegiline would be required for the same MAO-B effect as 1.8 mg of selegiline. In rats, Barbe reported R(−)desmethylselegiline to be an irreversible inhibitor of MAO-B, with a potency about 60 fold lower than selegiline in vitro and about 3 fold lower ex vivo (Barbe, H. O., *J. Neural Trans.* (Suppl.):32:131 (1990)).

The various diseases and conditions for which selegiline is disclosed as being to be useful include: depression (U.S. Pat. No. 4,861,800); Alzheimer's disease and Parkinson's disease, particularly through the use of transdermal dosage forms, including ointments, creams and patches; macular degeneration (U.S. Pat. No. 5,242,950); age-dependent degeneracies, including renal function and cognitive function as evidenced by spatial learning ability (U.S. Pat. No. 5,151,449); pituitary-dependent Cushing's disease in humans and nonhumans (U.S. Pat. No. 5,192,808); immune system dysfunction in both humans (U.S. Pat. No. 5,387,615) and animals (U.S. Pat. No. 5,276,057); age-dependent weight loss in mammals (U.S. Pat. No. 5,225,446); and schizophrenia (U.S. Pat. No. 5,151,419). PCT Published Application WO 92/17169 discloses the use of selegiline in the treatment of neuromuscular and neurodegenerative disease and in the treatment of CNS injury due to hypoxia, hypoglycemia, ischemic stroke or trauma. In addition, the biochemical effects of selegiline on neuronal cells have been extensively studied. For example, see Tatton, et al., "Selegiline Can Mediate Neuronal Rescue Rather than Neuronal Protection," *Movement Disorders* 8 (Supp. 1):S20–S30 (1993); Tatton, et al., "Rescue of Dying Neurons," *J. Neurosci. Res.* 30:666–672 (1991); and Tatton, et al., "(−)-Deprenyl Prevents Mitochondrial Depolarization and Reduces Cell Death in Trophically-Deprived Cells," 11th Int'l Symp. on Parkinson's Disease, Rome, Italy, Mar. 26–30, 1994.

Although selegiline is reported as being effective in treating the foregoing conditions, neither the precise number or nature of its mechanism or mechanisms of action are known. However, there is evidence that selegiline provides neuroprotection or neuronal rescue, possibly by reducing oxidative neuronal damage, increasing the amount of the enzyme superoxide dismutase, and/or reducing dopamine catabolism. For example, PCT Published Application WO 92/17169 reports that selegiline acts by directly maintaining, preventing loss of, and/or assisting in, the nerve function of animals.

Selegiline is disclosed as being useful when administered to a subject through a wide variety of routes of administration and dosage forms. For example U.S. Pat. No. 4,812,481 (Degussa AG) discloses the use of concomitant selegiline-amantadine in oral, peroral, enteral, pulmonary, rectal, nasal, vaginal, lingual, intravenous, intraarterial, intracardial, intramuscular, intraperitoneal, intracutaneous, and subcutaneous formulations. U.S. Pat. No. 5,192,550 (Alza Corporation) describes a dosage form comprising an outer wall impermeable to selegiline but permeable to external fluids. This dosage form may have applicability for the oral, sublingual or buccal administration of selegiline. Similarly, U.S. Pat. No. 5,387,615 discloses a variety of selegiline compositions, including tablets, pills, capsules, powders, aerosols, suppositories, skin patches, parenterals, and oral liquids, including oil-aqueous suspensions, solutions, and emulsions. Also disclosed are selegiline-containing sustained release (long acting) formulations and devices.

The present invention is directed to the novel, S(+) enantiomeric form of desmethylselegiline. This isomer has striking and wholly unexpected pharmacological effects and, accordingly, is surprisingly and unexpectedly useful in treating selegiline-responsive diseases and conditions. Assay results suggest that, in at least some respects, the S(+) enantiomer is considerably more effective than either selegiline or the R(−) enantiomer of desmethylselegiline. For example, results suggest that the S(+) enantiomer may be 4–5 times more effective than these other agents at inhibiting dopamine re-uptake by neurons and, in certain cell culture models, it has a greater neuroprotective effect than either R(−)desmethylselegiline or selegiline. Thus, the S(+) isomer is the form of choice in the treatment of conditions which require enhanced synaptic dopamine activity or neuronal protection/rescue. Such conditions include Parkinson's disease; Alzheimer's disease and attention deficit hyperactivity disorder (ADHD); dementia; depression; schizophrenia; and dysautonomia.

SUMMARY OF THE INVENTION

The present invention provides in part:

(a) a composition comprising the S(+) enantiomer of desmethylselegiline, a compound of the formula:

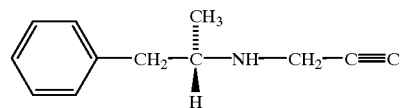

including the S(+) enantiomer in substantially isomerically pure form;

(b) a pharmaceutical composition comprising the S(+) enantiomer of desmethylselegiline, wherein one or more unit doses of said composition, administered on a periodic basis, are effective to treat a selegiline-responsive disease or condition in a animal to whom said unit dose or unit doses are administered;

(c) in a method for obtaining a selegiline-like therapeutic effect in a subject suffering from a selegiline-responsive disease or condition, the improvement which comprises:
   administering to said subject the S(+) enantiomer of desmethylselegiline in a dosage regimen sufficient to produce said selegiline-like therapeutic effect.

(d) a method of treating a condition in a mammal produced by neuronal degeneration, neuronal trauma or by a hypodopaminergic condition which comprises administering to said mammal the S(+) enantiomer of desmethylselegiline or a pharmaceutically acceptable acid addition salt thereof, at a daily dose, administered in a single or multiple dosage regimen, of at least about 0.015 mg, calculated on the basis of the free secondary amine, per kg of the mammal's body weight;

(e) a transdermal delivery composition for use in treating a condition in a mammal produced by neuronal degeneration, neuronal trauma or due to a hypodopaminergic condition which comprises a layered composite containing in at least one layer an amount of the S(+)

enantiomer of desmethylselegiline, or a pharmaceutically acceptable acid addition salt thereof, a sufficient to supply a daily transdermal dose of at least about 0.015 mg of the free secondary amine, per kg of the mammal's body weight; and (f) a method of treating a condition in a mammal produced by immune system dysfunction, which comprises administering to the mammal the S(+) enantiomer of desmethylselegiline, or a pharmaceutically acceptable acid addition salt thereof, at a daily dose, administered in a single or multiple dosage regimen, of at least about 0.015 mg, calculated on the basis of the free secondary amine, per kg of the mammal's body weight.

The present invention is based upon the discovery that both desmethylselegiline ("DMS" or "R(−)DMS") and its enantiomer (ent-desmethylselegiline, abbreviated as "ent-DMS" or "S(+)DMS") are useful in providing selegiline-like effects in subjects, notwithstanding dramatically reduced MAO-B inhibitory activity and an apparent lack of enhanced selectivity for MAO-B compared to selegiline. It has been discovered that desmethylselegiline, ent-desmethylselegiline and their isomeric mixtures provide a more advantageous way of obtaining selegiline-like therapeutic effects in selegiline-responsive diseases or conditions. This, is particularly true for diseases or conditions characterized by neuronal degeneration, neuronal trauma or which are hypodopaminergic in nature, i.e. diseases or conditions characterized by reduced dopamine release and formation.

Thus, the present invention is directed to compositions comprising the S(+) enantiomer of desmethylselegiline either alone or together with the R(−) enanatiomer. In preferred embodiments, the S(+) enantiomer is present at a greater concentration than the concentration of the R(−) enantiomer or, alternatively, in substantially isomerically pure form. S(+) and R(−) forms of desmethylselegiline can be conveniently prepared by methods known in the art, as described below in Example 1. The characteristics of a preparation of purified S(+) enantiomer have been determined and are described in Example 3. Its chemical structure is as follows:

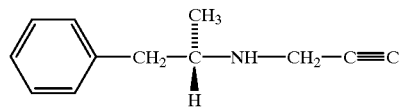

The S(+) enantiomer, S(+)DMS, is used as an active ingredient in novel pharmaceutical compositions. In this regard, a quantity of the isomer is employed such that one or more unit doses of the composition is effective in the treatment of one or more selegiline-responsive diseases or conditions in a subject administered toe composition on a periodic basis. If desired, the R(−) enantiomer may be included. Compositions may be designed so that they are suitable for oral, topical, transdermal, sublingual, buccal, parenteral or other conventional routes of administration. So formulated and administered, S(+)DMS compositions are useful for effecting an increase in dopaminergic activity, neuronal rescue/protection and can be administered in a manner so as to improve immune system function in a subject or to treat hypodopaminergic related diseases.

In addition, the present invention provides for an improved method for obtaining a selegiline-like therapeutic effect in a subject suffering from a selegiline-responsive disease or condition, which comprises administering to the subject the S(+) enantiomer of desmethylselegiline in an amount sufficient to produce the selegiline-like therapeutic effect. The S(+)DMS may be present in substantially isomerically pure form, a form preferred for the treatment of ADHD, or it may be present together with R(−)DMS.

As used herein the term "selegiline-responsive disease or condition" refers to any of the various diseases or conditions in mammals, including humans, for which selegiline is disclosed in the prior art as being useful. In particular, a "selegiline-responsive disease or condition" refers to the various diseases and conditions described above, e.g., Alzheimer's disease, cognitive dysfunction, neuronal rescue or protection, and the like. The term also refers to the use of selegiline as an appetite suppressant. Similarly, the term "selegiline-like therapeutic effect" refers to one or more of the salutary effects reported as being exerted by selegiline in subjects being treated for a selegiline-responsive disease or condition.

The selegiline-responsive diseases or conditions related to neuronal degeneration or trauma which respond to the present methods include Parkinson's disease, Alzheimer's disease, depression, glaucoma, macular degeneration, ischemia, diabetic neuropathy, attention deficit disorder, post polio syndrome, multiple sclerosis, impotence, narcolepsy, chronic fatigue syndrome, alopecia, senile dementia, hypoxia, cognitive dysfunction, negative symptomatology of schizophrenia, amyotrophic lateral sclerosis, Tourette's syndrome, tardive dyskinesia, and toxic neurodegeneration.

In preferred embodiments, the invention is directed to a method of treating a mammal for a hypodopaminergic condition or neuronal trauma/neuronal degeneration by administering the S(+) enantiomer of desmethylselegiline, or a pharmaceutically acceptable acid addition salt of this enantiomer, at a daily dose of at least about 0.015 mg per kg body weight. The dosage is based upon the weight of the free secondary amine and may be administered in either a single or multiple dosage regimen.

The present invention also encompasses the restoration or improvement of immune system function by S(+)DMS. Again, the S(+) enantiomer may be administered either as a substantially pure isomer or in combination with R(−)DMS. The conditions or diseases treatable include age-dependent immune system dysfunction, AIDS, immunological loss due to cancer chemotherapy and infectious diseases. In a preferred embodiment, the invention is directed to a method of treating a condition in a mammal produced by immune system dysfunction, by administering the S(+) enantiomer of desmethyl-selegiline, or a pharmaceutically acceptable acid addition salt thereof, at a daily dose of at least about 0.015, mg, calculated on the basis of the free secondary amine, per kg of the mammal's body weight.

Depending upon the particular route employed, desmethylselegiline is administered in the form of a free base or as a physiologically acceptable non-toxic acid addition salt. Acid addition salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like. The use of salts, especially the hydrochloride, is particularly desirable when the route of administration employs aqueous solutions, as for example parenteral administration. Use of delivered S(+)-desmethylselegiline, in the form of the free base is especially useful for transdermal administration. Reference herein to the administration of DMS or ent-DMS or to mixtures thereof encompasses both the free base and acid addition salt forms.

The optimal daily dose of S(+)-desmethylselegiline useful for the purposes of the present invention is determined by methods known in the art, e.g., based on the severity of the disease or condition being treated, the condition of the subject to whom treatment is being given, the desired degree of therapeutic response, and the concomitant therapies being administered to the patient or animal. Ordinarily, however, the attending physician or veterinarian will administer an initial dose of at least about 0.015 mg/kg, calculated on the basis of the free secondary amine, with progressively higher doses being employed depending upon the route of administration and the subsequent response to the therapy. Typically the daily dose will be about 0.10 mg/kg and may extend to about 1.0 mg/kg of the patient's body weight (all such doses again being calculated on the basis of the free secondary amine). These guidelines further require that the actual dose be carefully titrated by the attending physician or veterinarian depending on the age, weight, clinical condition, and observed response of the individual patient or animal.

The daily dose can be administered in a single or multiple dosage regimen. Oral dosage forms will most typically be used and are preferred but other dosage forms may also be employed and may permit, for example, a continuous release of relatively small amounts of the active ingredient from a single dosage unit, such as a transdermal patch, over the course of one or more days. This is particularly desirable in the treatment of chronic conditions such as Parkinson's disease, Alzheimer's disease, and depression. Alternatively, it may be desirable in conditions such as ischemia or neural damage to administer one or more discrete doses by a more direct systemic route such as intravenously or by inhalation. In still other instances such as glaucoma and macular degeneration, localized administration, such as via the intraocular route, can be indicated.

Pharmaceutical compositions containing S(+)-desmethylselegiline can be prepared according to conventional techniques. For example, preparations for parenteral routes of administration of S(+)-desmethylselegiline, e.g., intramuscular, intravenous and intraarterial routes, can employ sterile isotonic saline solutions. Sterile isotonic buffered solutions can also be employed for intraocular administration.

Transdermal dosage unit forms of S(:+)-desmethylselegiline can be prepared utilizing a variety of previously described techniques (see e.g., U.S. Pat. Nos. 4,861,800; 4,868,218; 5,128,145; 5,190,763; and 5,242,950; and EP-A 404807, EP-A 509761, and EP-A 593807). For example, a monolithic patch structure can be utilized in which S(+)-desmethylselegiline is directly incorporated into the adhesive and this mixture is cast onto a backing sheet. Alternatively S(+)-desmethylselegiline, can be incorporated as an acid addition salt into a multilayer patch which effects a conversion of the salt to the free base, as described for example in EP-A 593807. In a preferred embodiment, the present invention is directed to a transdermal delivery composition for use in treating a condition in a mammal produced by neuronal degeneration or neuronal trauma and for treating hypodopaminergic diseases.

Subjects treatable by the present preparations and methods include both human and non-human subjects for which selegiline-like therapeutic effects are known to be useful. Accordingly, the compositions and methods above provide especially useful therapies for mammals, especially domesticated mammals. Thus, the present methods and compositions are used in treating selegiline-responsive diseases or conditions in canine and feline species.

Successful use of the compositions and methods above requires employment of an effective amount of S(+)-desmethylselegiline. Although both R(−) desmethylselegiline and S(+)-desmethylselegiline are dramatically less potent than selegiline as inhibitors of MAO, employment of these agents, or a mixture of these agents, does not require a commensurately increased dosage to obtain a selegiline-like therapeutic response. Surprisingly, dosages necessary to attain a selegiline-like therapeutic effect appear to be on the same order as the known doses of selegiline. Accordingly, because both desmethylselegiline and ent-desmethylselegiline exhibit a much lower inhibition of MAO-A at such dosages, desmethylselegiline and ent-desmethylselegiline provide a substantially wider margin of safety with respect to MAO-A associated toxicity compared to selegiline. In particular, the risk of the adverse effects of MAO-A inhibition, e.g., hypertensive crisis, are minimized due to the reduced potency for MAO-A inhibition.

As described above and notwithstanding its demonstrably inferior inhibitory properties with respect to MAO-B inhibition, S(+)-desmethylselegiline appears to be at least as effective as selegiline in treating certain selegiline-responsive conditions, e.g., conditions resulting from reduced dopamine release and formation, neuronal degeneration or neuronal trauma. Although the oral route of administration will generally be most convenient, drug may be administered by the parenteral, topical, transdermal, intraocular, buccal, sublingual, intranasal, inhalation, vaginal, rectal or other routes as well.

DETAILED DESCRIPTION OF THE INVENTION

Figure 1:
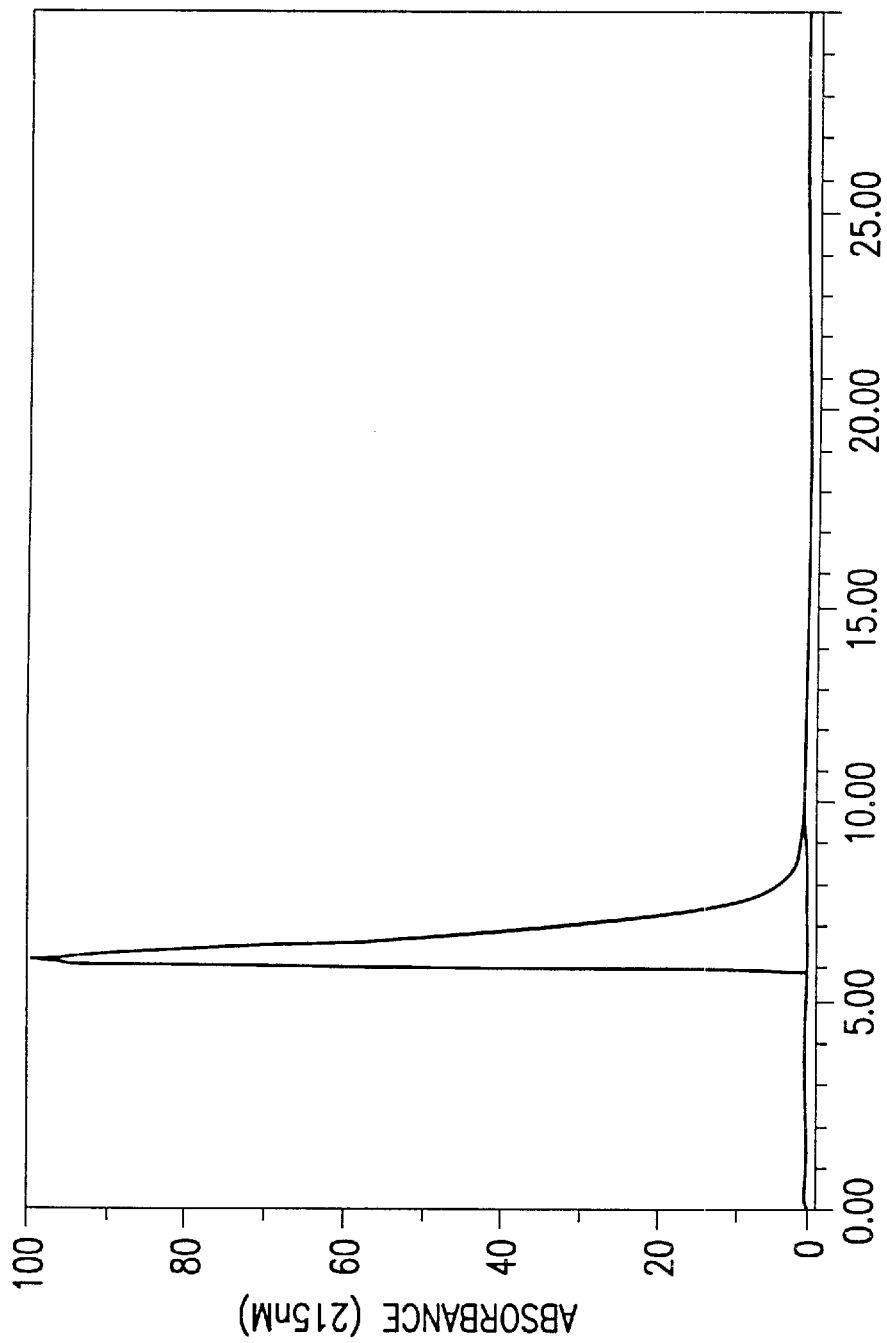
FIG. 1: HPLC Chromatogram of Purified R(−)DMS (Microsorb MV Cyano Column). The purity of a preparation of R(−)DMS was determined by RPLC on a Microsorb MV Cyano column and results are shown in FIG. 1. The column had dimensions of 4.6 mm×15 cm and was developed at a flow rate of 1.0 ml/min using a mobile phase containing 90% 0.01 M $H_3PO_4$(pH 3.5) and 10% acetonitrile. The column was run at a temperature of 40° C. and effluent was monitored at a wavelength of 215 nm. The chromatogram shows one major peak appearing at a time of 6.08 minutes and having 99.5% of the total light-absorbing material eluted from the column. No other peak had greater than 0.24%.

The surprising utility of S(+)desmethylselegiline and desmethylselegiline in treating certain selegiline-responsive diseases or conditions is attributable in part to their powerful action in preventing loss of dopaminergic neurons by promoting repair and recovery. Hence, at doses at which little or no MAO-B inhibition is generally observed, a reversal in neuronal damage and/or death can be observed. Because S(+)-desmethylselegiline is a more potent inhibitor of dopamine uptake and also can prevent loss and facilitate recovery of nerve cell function, it is of value in a wide variety of hypodopaminergic, neurodegenerative and neuromuscular diseases. In this regard, S(+)DMS is substantially more potent than R(−)desmethylselegiline, selegiline in certain pharmacological effects, as described more empirically in the examples below.

EXAMPLES

Example 1

Preparation of Desmethylselegiline and Ent-desmethylselegiline

A. Desmethylselegiline

Desmethylselegiline (designated below as "R(−)DMS") is prepared by methods known in the art. For example, desmethylselegiline is a known chemical intermediate for the preparation of selegiline as described in U.S. Pat. No. 4,925,878. Desmethylselegiline can be prepared by treating a solution of R(−)-2-aminophenylpropane (levoamphetamine):

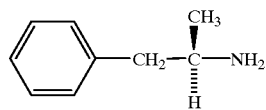

in an inert organic solvent such as toluene with an equimolar amount of a reactive propargyl halide such as propargyl bromide, Br—$CH_2$—C≡CH, at slightly elevated temperatures (70°–90° C.). Optionally the reaction can be conducted in the presence of an acid acceptor such as potassium carbonate. The reaction mixture is then extracted with aqueous acid, for example 5% hydrochloric acid, and the extracts are rendered alkaline. The nonaqueous layer which forms is separated, for example by extraction with benzene, dried, and distilled under reduced pressure.

Alternatively the propargylation can be conducted in a two-phase system of a water-immiscible solvent and aqueous alkali, utilizing a salt of R(+)-2-aminophenylpropane with a weak acid such as the tartrate, analogously to the preparation of selegiline as described in U.S. Pat. No. 4,564,706.

B. Ent-Desmethylselegiline

Ent-desmethylselegiline (designated below as "S(+) DMS") is conveniently prepared from the enantiomeric S(+)-2-aminophenylpropane (dextroamphetamine), i.e.,

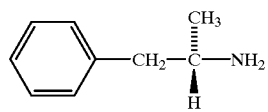

following the procedures set forth above for desmethylselegiline.

C. Mixtures of Enantiomers

Mixtures of enantiomeric forms of desmethylselegiline, including racemic desmethylselegiline, are conveniently prepared from enantiomeric mixtures, including racemic mixtures of the above aminophenylpropane starting material.

D. Conversion Into Acid Addition Salts

N-(prop-2-ynyl)-2-aminophenylpropane in either optically active or racemic form can be converted to a physiologically acceptable non-toxic acid addition salt by conventional techniques such as treatment with a mineral acid. For example, hydrogen chloride in isopropanol is employed in the preparation of desmethylselegiline hydrochloride. Either the free base or salt can be further purified, again by conventional techniques such as recrystallization or chromatography.

Example 2

Characteristics of Substantially Pure R(−)DMS

Figure 2:
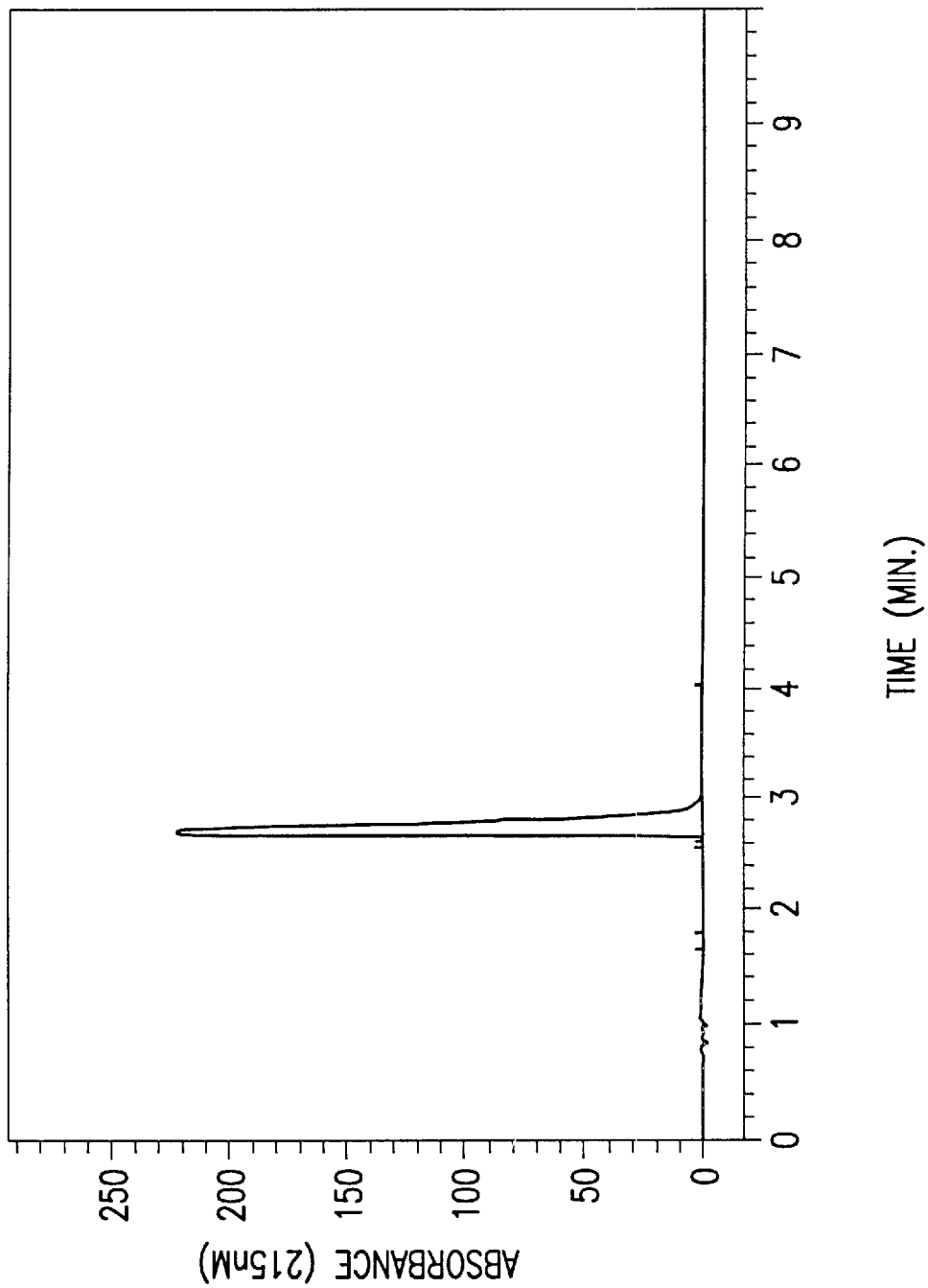
FIG. 2: HPLC Elution Profile of R(−)DMS (Zorbax Mac-Mod C18 Column). The same preparation that was analyzed in the experiments discussed in FIG. 1 was also analyzed for purity by HPLC on a Zorbax Mac-Mod SB-C18 column (4.6 mm×75 mm). Effluent was monitored at 215 nm and results can be seen in FIG. 2. Greater than 99.6% of the light-absorbing material appeared in the single large peak eluting at a time of between 2 and 3 minutes.
Figure 3:
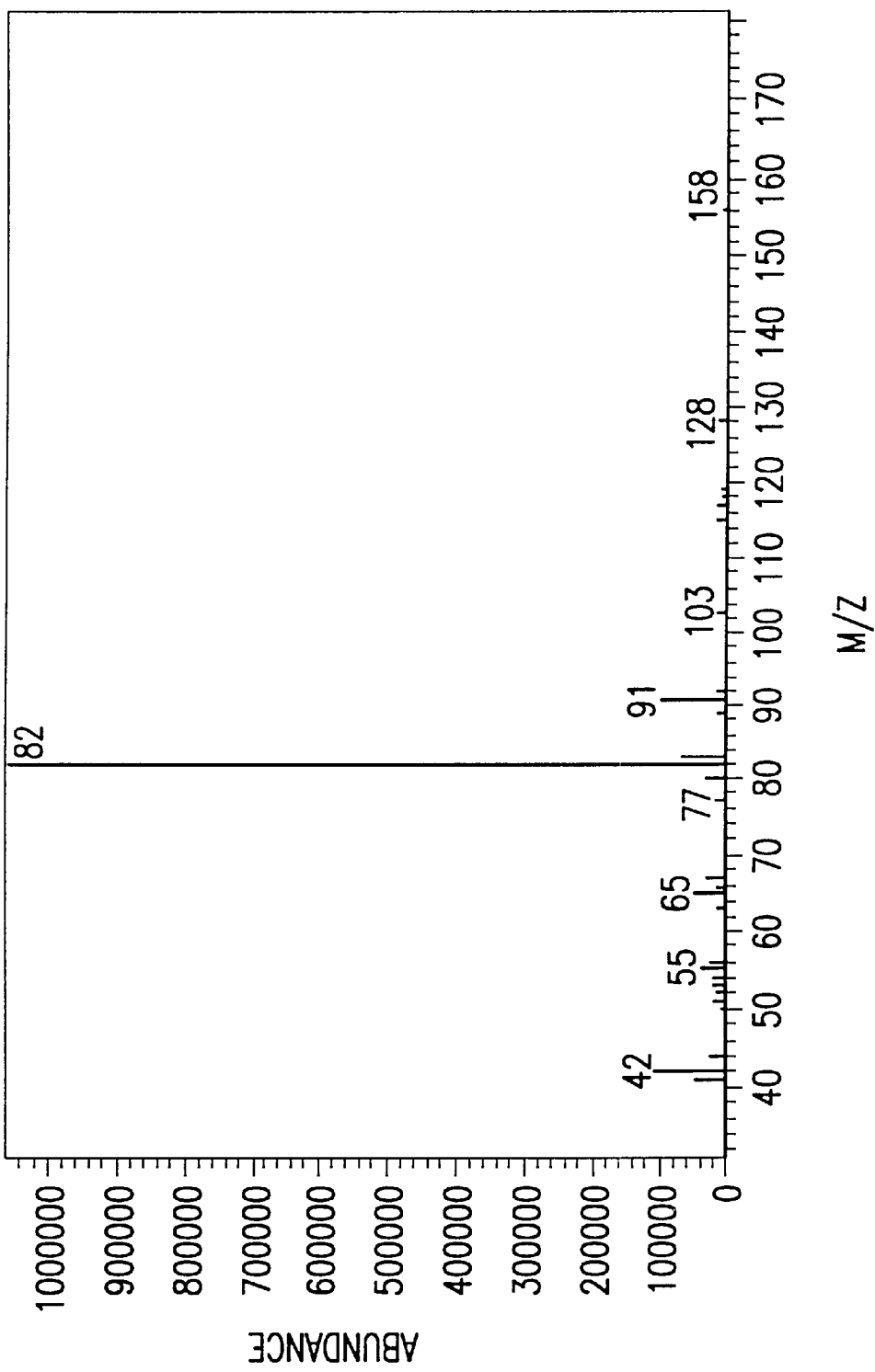
FIG. 3: Mass Spectrum of R(−)DMS. A mass spectrum was obtained for purified R(−)DMS and results are shown in FIG. 3. The spectrum is consistent with a molecule having a molecular weight of 209.72 and a molecular formula of $C_{12}H_{15}N.HCl$.
Figure 4:
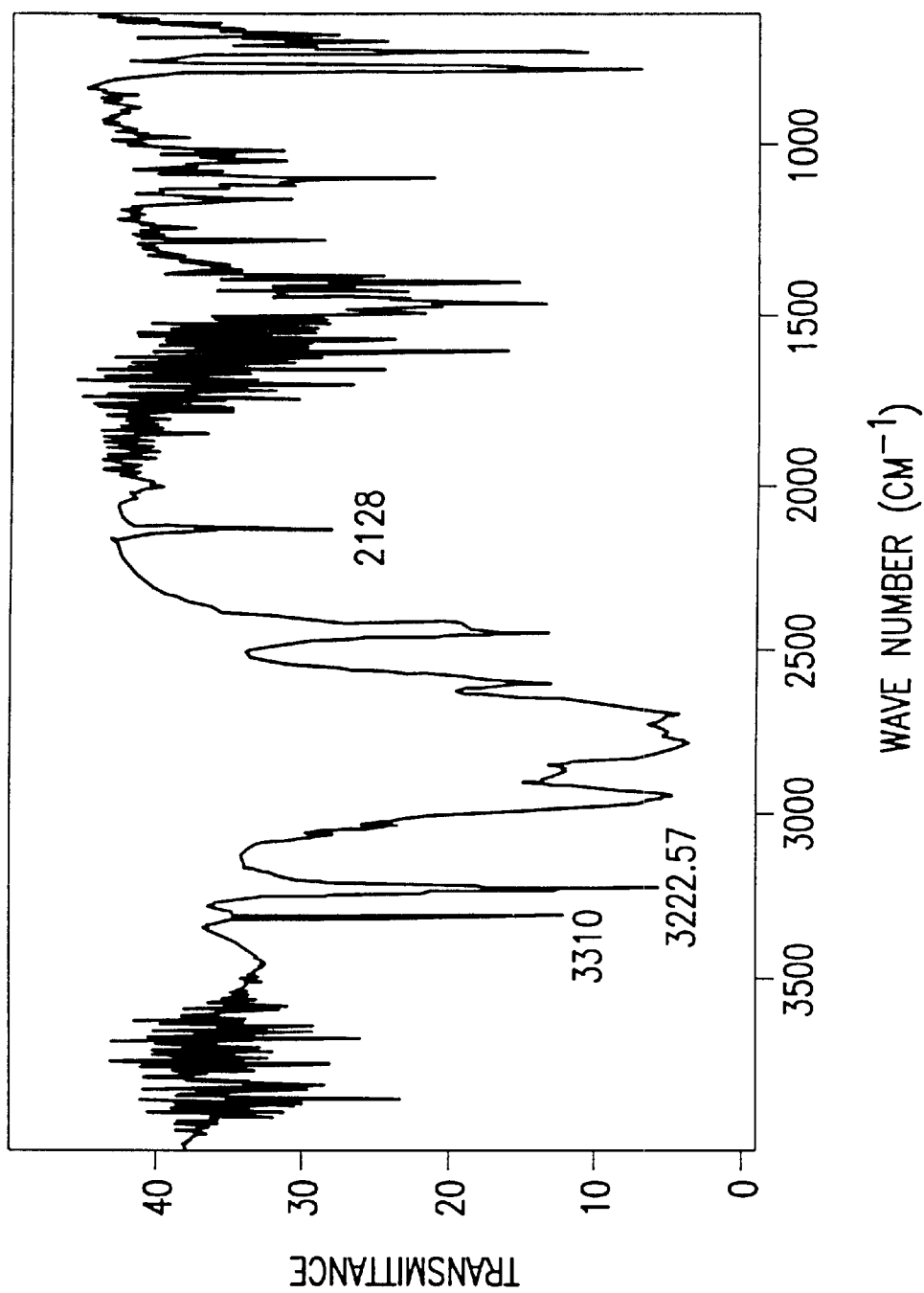
FIG. 4: Infrared Spectrum (KBr) of Purified R(−)DMS. Infrared spectroscopy was performed on a preparation of R(−)DMS and results are shown in FIG. 4. The solvent used was $CDCl_3$.
Figure 5:
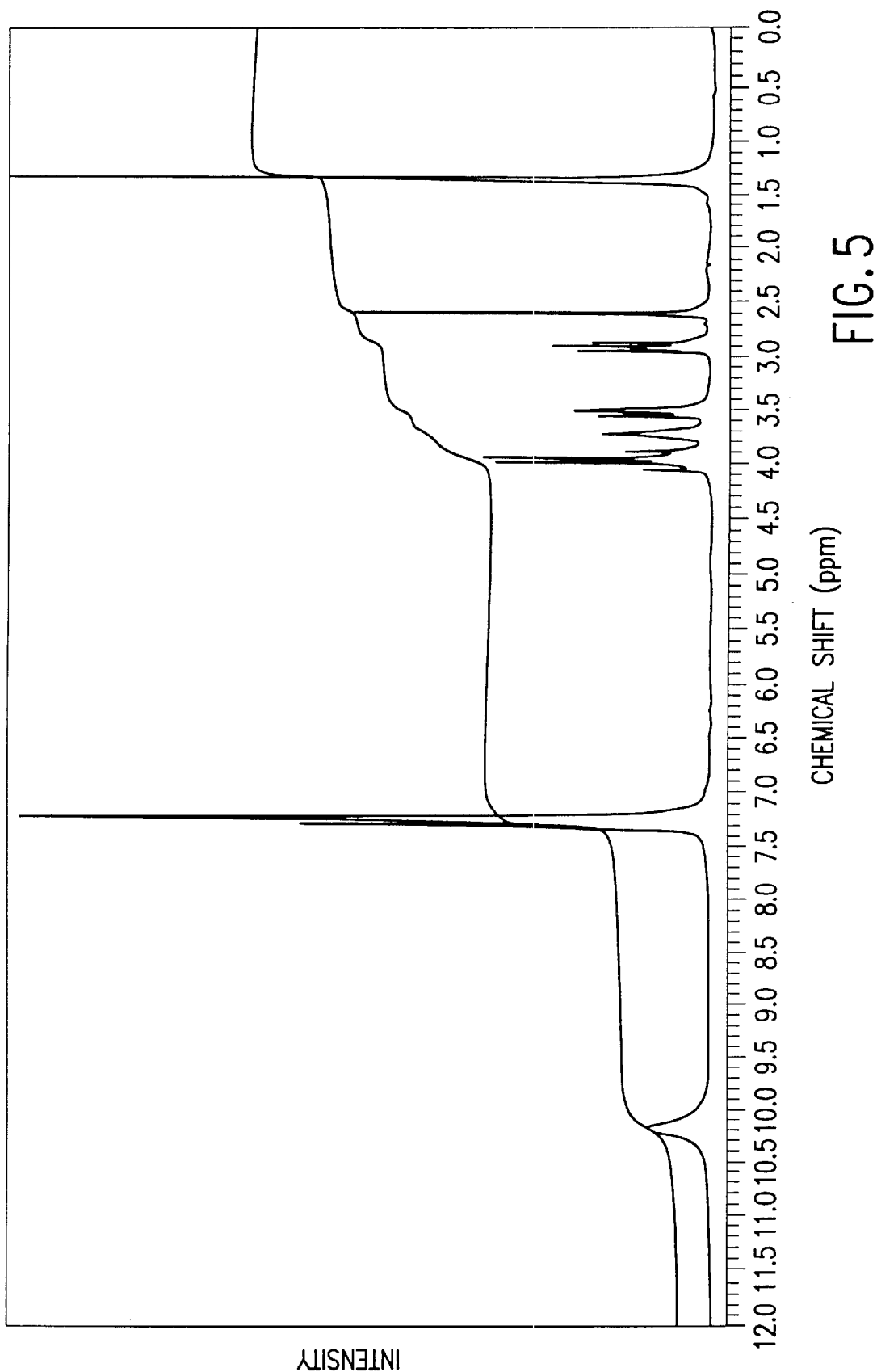
FIG. 5: NMR Spectrum of Purified R(−)DMS. A preparation Purified R(−)DMS was dissolved in $CDCl_3$ and H NMR spectroscopy was performed at 300 MHZ. Results are shown in FIG. 5.

A preparation of substantially pure R(−)DMS has the appearance of a white crystalline solid with a melting point of 162–163° C. and an optical rotation of $[\alpha]_D^{23°\,C.}=-15.2+/-2.0$ when measured at a concentration of 1.0 M using water as solvent. R(−)DMS appeared to be 99.5% pure when analyzed by HPLC on a Microsorb MV Cyano column (see chromatogram in FIG. 1) and 99.6% pure when analyzed by HPLC on a Zorbax Mac-Mod SB-C18 column (see chromatogram in FIG. 2). No single impurity is present at a concentration greater than or equal to 0.5%. Heavy metals are present at a concentration of less than 10 ppm and amphetamine hydrochloride at a concentration of less than 0.03%. The last solvents used for dissolving the preparation, ethyl acetate and ethanol are both present at a concentration of less than 0.1%. A mass spectrum performed on the preparation (see FIG. 3) is consistent with a compound having a molecular weight of 209.72 and a formula of $C_{12}H_{15}N.HCl$. Infrared and NMR spectra are shown in FIGS. 4 and 5 respectively. These are also consistent with the known structure of R-(−)-DMS.

Example 3

Characteristics of Substantially Pure S(+)DMS

Figure 6:
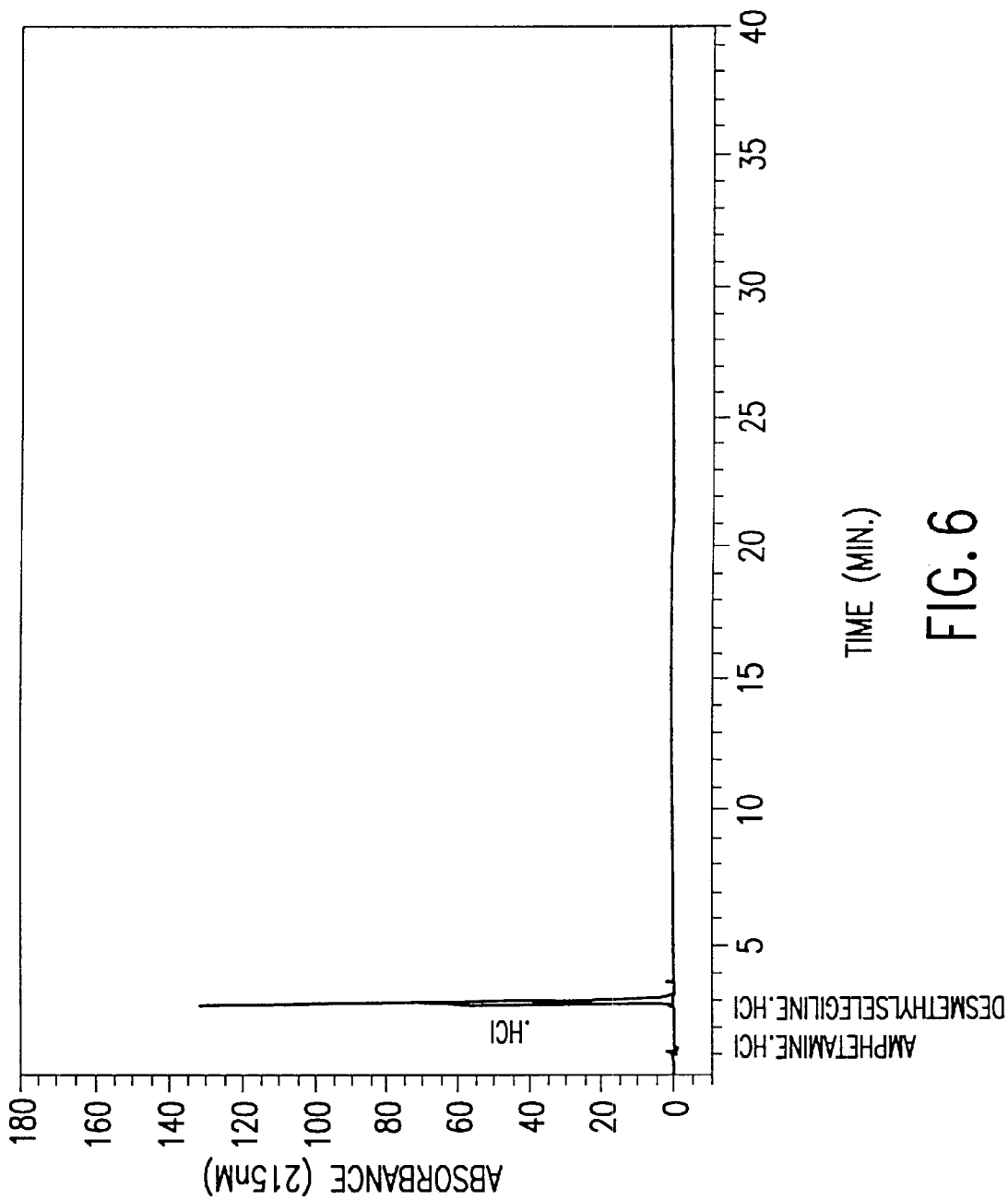
FIG. 6: HPLC Chromatogram of S(+)DMS. The purity of a preparation of S(+)DMS was examined by reverse phase HPLC on a 4.6 mm×75 mm Zorbax Mac-Mod SB-C18 column. The elution profile, monitored at 215 nm, is shown in FIG. 6. One major peak appears in the profile at a time of about 3 minutes and contains greater than 99% of the total light-absorbing material that eluted from the column.
Figure 7:
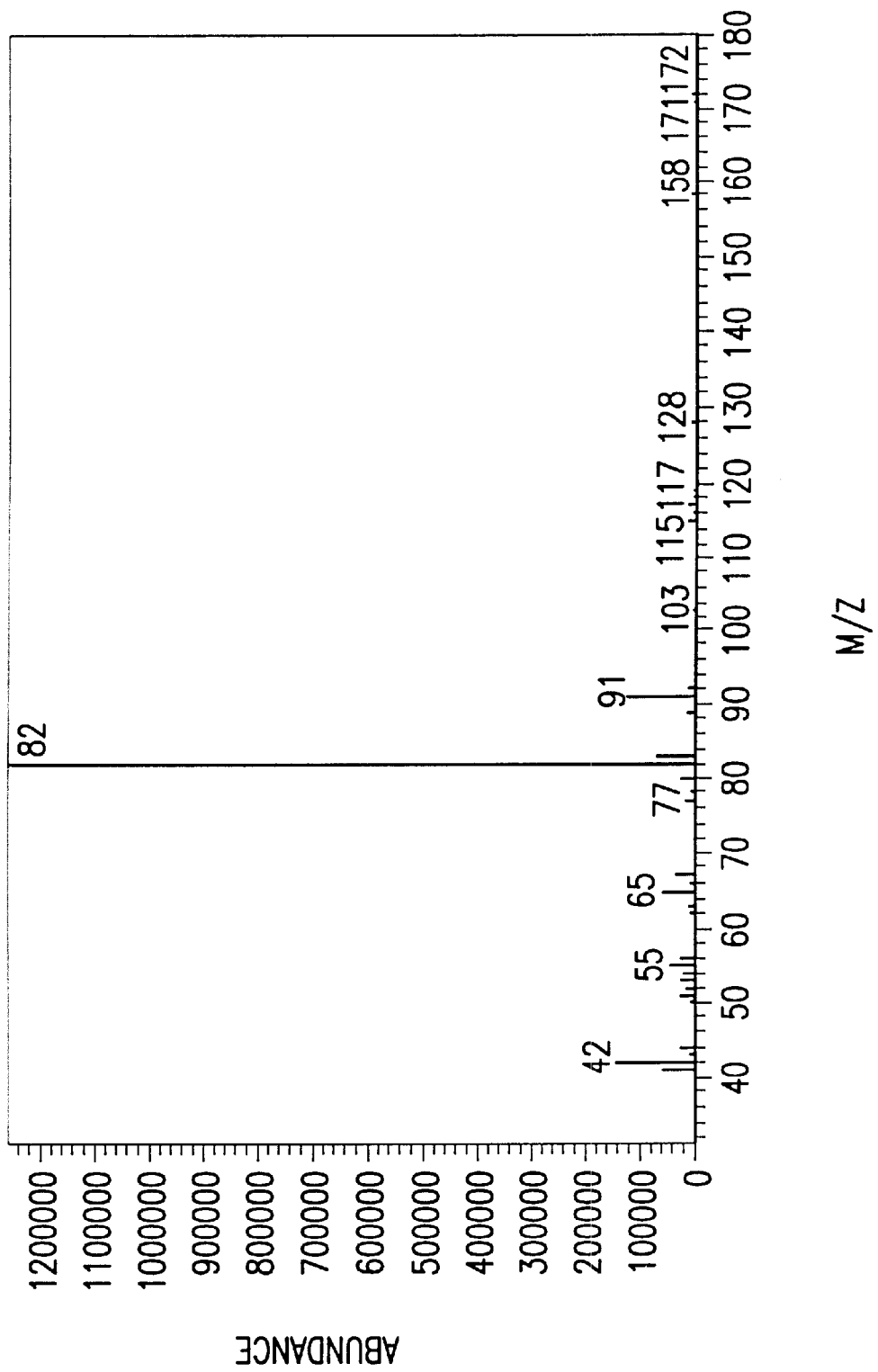
FIG. 7: Mass Spectrum of Purified S(+)DMS. Mass spectroscopy was performed on the same preparation examined in FIG. 6. The spectrum is shown in FIG. 7 and is consistent with the structure of S(+)DMS.
Figure 8:
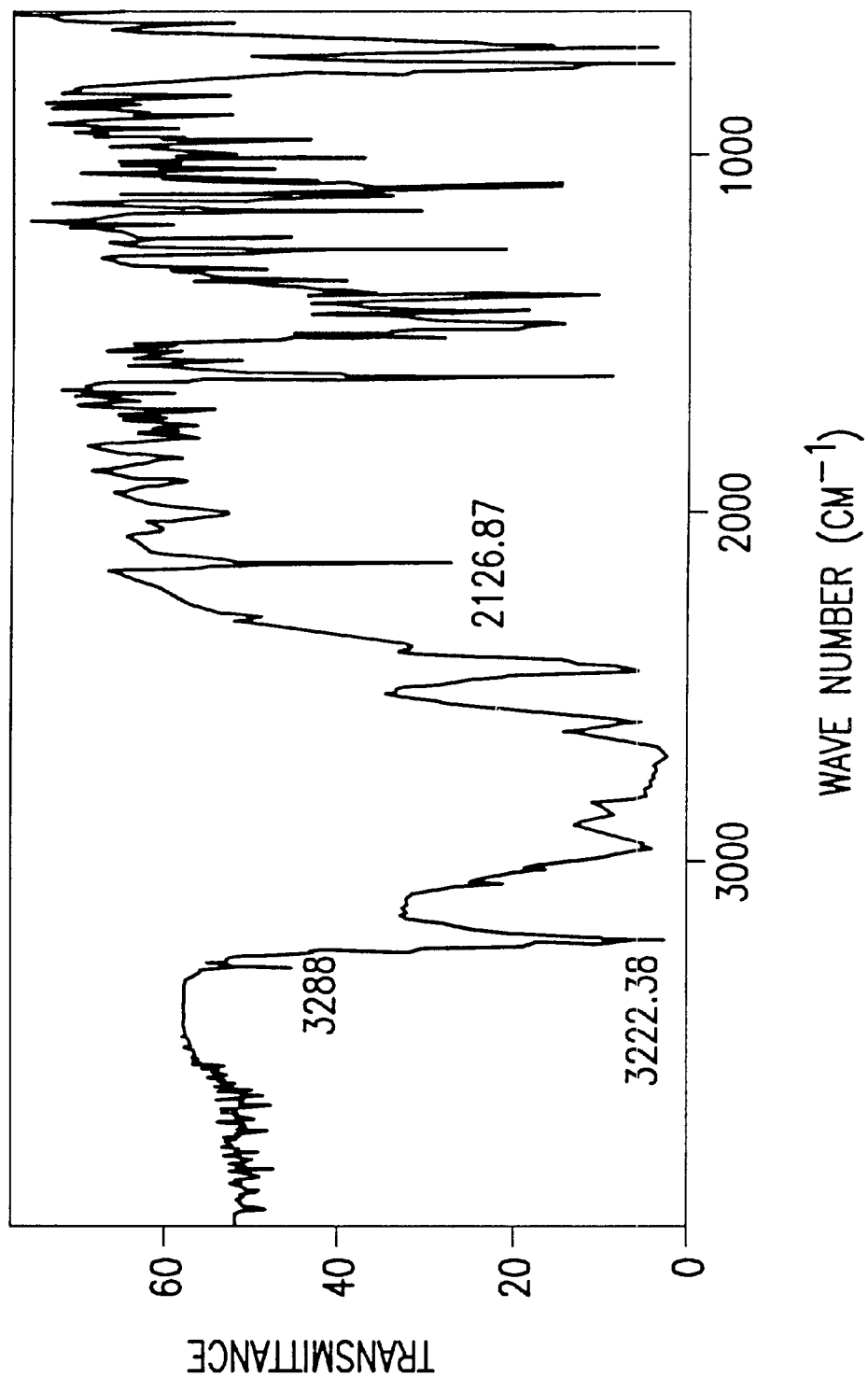
FIG. 8: Infrared Spectrum (KBr) of Purified S(+)DMS. The preparation of S(+)DMS discussed in connection with FIGS. 6 and 7 was examined by infrared spectroscopy and results are shown in FIG. 8.

A preparation of substantially pure S(+)DMS has the appearance of a white powder with a melting point of approximately 160.04° C. and a specific rotation of +15.1 degrees when measured at 22° C. in water, at a concentration of 1.0 M. When examined by reverse phase HPLC on a Zorbax Mac-Mod SB-C18 column the preparation appears to be about 99.9% pure (FIG. 6). Amphetamine hydrochloride is present at a concentration of less than 0.13% (w/w). A mass spectrum is performed on the preparation and is consistent with a compound having a molecular weight of 209.72 and a molecular formula of $C_{12}H_{15}N.HCl$. (see FIG. 7). Infrared spectroscopy is performed and also provides results consistent with the structure of S(+)DMS (see FIG. 8).

Example 4

Neuronal Survival as Measured Using Tyrosine Hydroxylase

The effect of desmethylselegiline on neuron survival can be correlated to tyrosine hydroxylase, the rate limiting enzyme in dopamine biosynthesis. Assays are performed by determining the number of tyrosine hydroxylase positive cells in cultured E-14 embryonic mesencephalic cells over a period of 7 to 14 days. Protection in this system has been seen with a W variety of trophic factors including BDNF, GDNF, EGF, and β-FGF.

A. Test Methods

Timed pregnant Sprague-Dawley rats are used to establish neuronal cultures from embryonic rat brain on the 14th day of gestation. Mesencephalon is dissected out without the membrane coverings and collected in $Ca^{++}$ and $Mg^{++}$ free balanced salt solution at 4° C. Tissue fragments are dissociated in chemically defined medium by mild trituration with a small bore pasteur pipette. Cell suspension is plated in polyomithine-coated 35 mm Falcon plastic dishes (0.1 mg/ml, Sigma) at a density of $1.5 \times 10^6$ cells/dish. Cultures are maintained at 37° C. in an atmosphere of 10% $CO_2$/90% air and 100% relative humidity, and fed twice weekly with chemically defined medium consisting of MEM/F12 (1:1, Gibco), glucose (33 mM), HEPES (15 mM), $NaHCO_3$ (44.6 mM), transferrin (100 mg/ml), insulin (25 mg/ml), putrescine (60 nM), sodium selenite (30 nM), progesterone (20 nM), and glutamine (2 mM). Control cells receive no further additions. The medium used for other cells also included test substance, e.g. selegiline, at one or more concentrations.

Cultures are fixed in 4% paraformaldehyde in 0.1 M phosphate buffer (pH 7.4) for 30 minutes at room temperature, permeabilized with 0.2% Triton X-100 for 30 minutes and incubated with an antibody against tyrosine hydroxylase (1:1000; Eugene Tech) for 48, hours at 4° C. in the presence of a blocking serum. They are then stained using a peroxidase-coupled avidin-biotin staining kit (Vectastain ABC kit; Vector Labs) with 3',3'-diaminobenzidine as a chromagen.

The number of doparninergic neurons in cultures is determined by counting the cells positively immunostained with TH antibodies. 100 fields (0.5 mm×0.5 mm) in two transverse strips across the diameter of the dish, representing 2.5% of the total area, are counted using a Nikon inverted microscope at 200× magnification.

B. Results

Using the procedures described above, the following results were obtained:

TABLE 2

Effect of Selegiline and DMS on the Survival of TH Positive Cells

| Conc. | Control Mean cells/cm² | Selegiline Mean cells/cm² | % cont. | Desmethylselegiline Mean cells/cm² | % cont. |
|---|---|---|---|---|---|
| 0.5 μM | 108.55 | 201.70 ± 25.01 | 185.81 | 246.00 ± 22.76 | 226.62 |
| 5 μM | — | 237.00 ± 12.59 | 218.33 | 357.95 ± 25.76 | 329.76 |
| 50 μM | — | 292.28 ± 17.41 | 269.25 | 391.60 ± 34.93 | 360.76 |

Example 5

Neuronal Survival as Measured Using Dopamine Uptake

In addition to determining the number of TH positive cells in culture (see Example 4) the protective effect of desmethylselegiline on neuronal cells also can be determined by directly measuring dopamine uptake. The amount of uptake by the cultured brain cells corresponds to axonal growth.

A. Test Methods

Cell cultures, established in the manner discussed above, are incubated with [$^3$H]dopamine (0.5 mCi/ml; 37 Ci/mmol; New England Nuclear) for 15 minutes in the presence of ascorbic acid (0.2 mg/ml) in PBS (pH 7.3), supplemented with 0.9 mM $CaCl_2$ and 0.5 mM $MgCl_2$ at 37° C. After two rinses and a 5 minute incubation with fresh buffer, [$^3$H] dopamine accumulated within the cells is released by incubating the cultures with 95% ethanol for 30 minutes at 37° C. Preparations are then added to 10 ml Ecoscint (National Diagnostics) and counted in a scintillation spectrometer. Nonspecific uptake values are obtained by blocking dopaminergic neuronal uptake with 10 mM mazindol.

B. Results

Using the above procedure, the results shown in Table 3 were obtained.

TABLE 3

Effect of Selegiline and DMS on $^3$H-Dopamine Uptake

| Conc. | Cont Mean | Selegiline Mean | % Cont | Desmethylselegiline Mean | % Cont |
|---|---|---|---|---|---|
| 0.5 μM | 11982 | 14452 ± 212 | 120.6 | 24020 ± 800 | 200.4 |
| 54 μM | — | 16468 ± 576 | 137.5 | 34936 ± 2119 | 291.5 |
| 50 μM | — | 33018 ± 1317 | 275.5 | 56826 ± 2656 | 474.3 |

C. Conclusions from Examples 4 and 5

The results described in Examples 4 and 5 indicate that desmethylselegiline is substantially more potent than selegiline as a neuroprotective agent. This is true notwithstanding the fact that desmethylselegiline in much less potent than selegiline as an inhibitor of MAO-B.

Example 6

Neuroprotective Action of Desmethylselegiline Enantiomers in Cultured Dopamine-Containing Mesencephalic Neurons In Vitro The survival of mesencephalic, dopamine-containing neuronal cultures of rat brain tissue was used in these experiments to examine neuroprotective properties of selegiline and R(–) desmethylselegiline. The number of TH positive neurons is directly proportional to the survival of dopaminergic neurons and $^3$H-dopamine uptake is a measure of axonal growth in these neurons.

A. Effect of Selegiline on the Survival of Dopaminergic Neurons.

Figure 9:
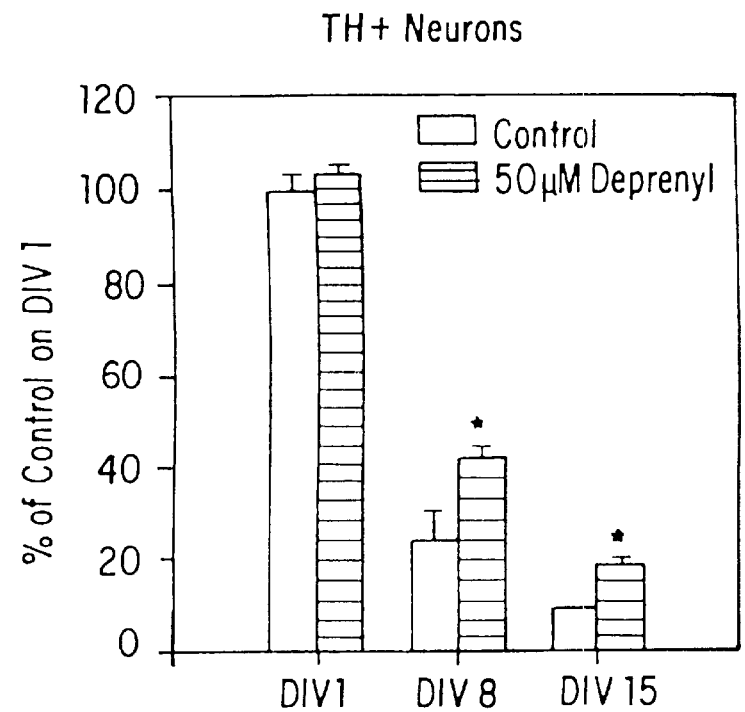
FIG. 9: Effect of Selegiline on Neuron Survival. Mesencephalic cultures were prepared from embryonic 14 day rats. Cultures were used at about 1.5 million cells per plate and were maintained either in growth medium alone (control cultures) or in growth medium supplemented with selegiline. On day 1, 8 and 15, cells were immunostained for the presence of tyrosine hydroxylase ("TH"). Striped bars represent results obtained for cultures maintained in the presence of 50 AM selegiline and open bars represent results for control cultures. In all cases, results are expressed as a percentage of TH positive cells present in control cultures on day 1. The abbreviation "DIV" refers to "days in vitro." Asterisks or stars above bars both in FIG. 9 and the figures discussed below indicates a result that differs from controls in an amount that is statistically significant, i.e. $P<0.05$.
Figure 10:
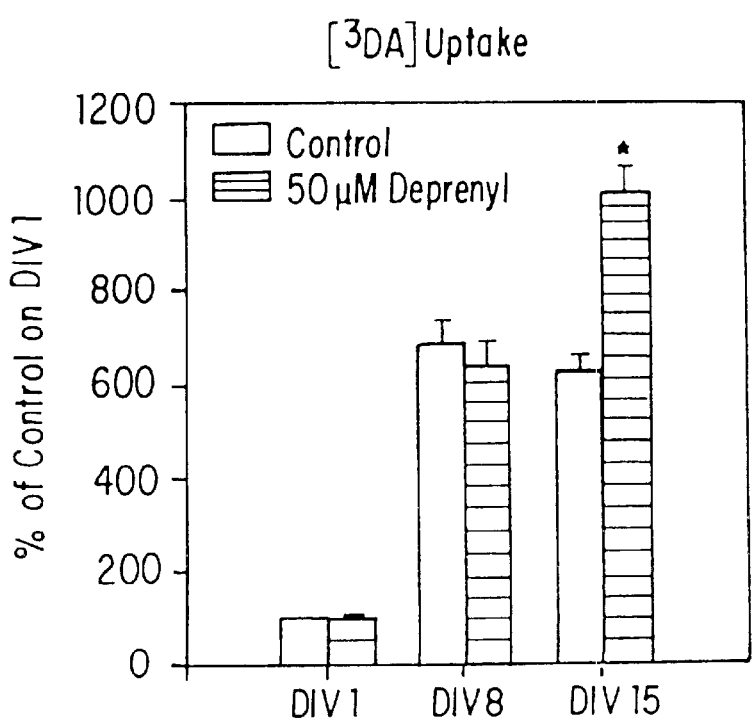
FIG. 10: [$^3$H]-Dopamine Uptake in Mesencephalic Cells. Cells, cultured as described, above for FIG. 9, were tested for their uptake of labeled dopamine and results are shown in FIG. 10. Striped bars represent uptake in cells maintained in the presence of 50 $\mu$M selegiline and open bars represent uptake in control cultures.

Mesencephalic cultures prepared from embryonic day 14 rats were treated with 0.5, 5 or 50 μM selegiline for 15 days, beginning on the day of plating. (For a more detailed discussion of the culturing of cells and other methods used in these experiments see Mytilineou et al., *J. Neurochem.* 61:1470–1478 (1993)). Survival and growth of dopamine neurons was evaluated by tyrosine hydroxylase (TH) immunocytochemistry and [$^3$H]dopamine uptake and results are shown in FIGS. 9 and 10.

B. Effect of Selegiline on Glutamate Receptor Dependent Cell Death.

Figure 11:
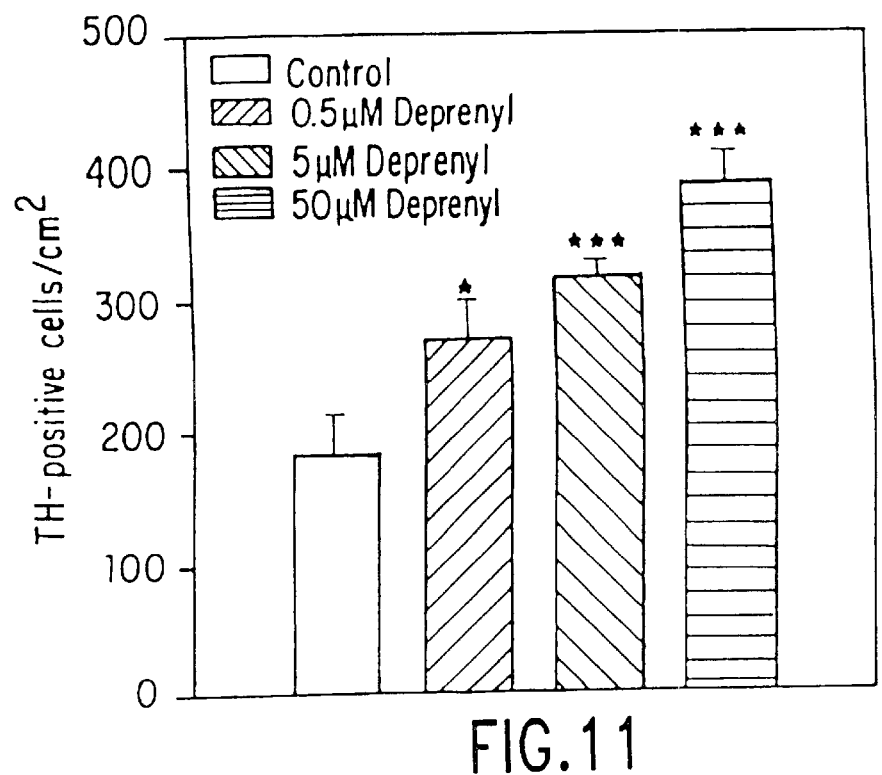
FIG. 11: Effect of Selegiline on Glutamate Receptor Dependent Neuronal Cell Death. Rat embryonic mesencephalic cells were cultured as described above. After allowing cultures to stabilize, the culture medium was changed daily for a period of 4 days to induce glutamate receptor-dependent cell death. Depending on the culture, medium contained either 0.5, 5.0 or 50 $\mu$M selegiline. After the final medium change, cultured cells were immunostained for the presence of tyrosine hydroxylase. From left to right, bars represent results for controls, 0.5, 5.0 and 50 $\mu$M selegiline.
Figure 12:
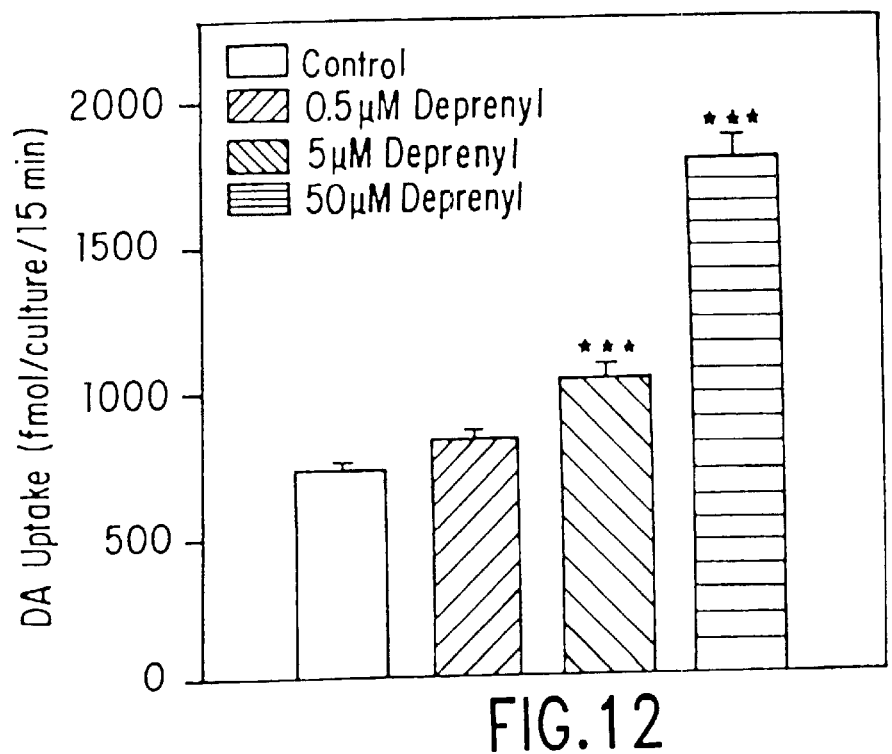
FIG. 12: Effect of Selegiline on Dopamine Uptake in Neuronal Cultures. Rat mesencephalic cells were cultured and medium was changed on a daily basis as discussed for FIG. 11. Uptake of tritiated dopamine by cells was measured and results are shown in the figure. From left to right, bars are in the same order as for FIG. 11.

The neuroprotective effect of selegiline was also examined using an experimental paradigm that causes neuronal cell death that can be blocked by inhibition of glutamate receptors. In these experiments, cells were plated and allowed to stabilize for several, days. The growth medium of the cells was then changed on a daily basis to induce cell death that can be prevented by blocking glutamate receptors, e.g. using MK-801. After 4 days of daily medium changes, cultures were stained for tyrosine hydroxylase and assayed for, uptake of tritiated dopamine. The results shown in FIGS. 11 and 12 further support the conclusion that selegiline promotes the survival of dopaminergic neurons.

C. Effect of Desmethylselegiline on the Survival of Dopamine Neurons.

Figure 13:
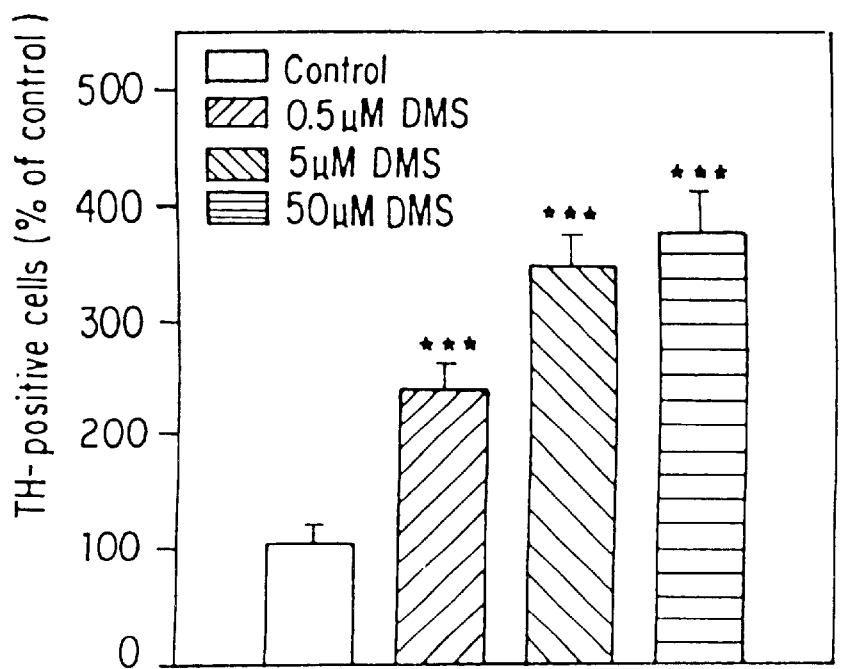
FIG. 13: Effect of R(-)Desmethylselegiline on Glutamate Receptor Dependent Neuronal Cell Death. Rat embryonic mesencephalic cultures were prepared as described above except that R(-)DMS was used instead of selegiline. On day 9, the number of TH positive cells in cultures was determined. Results are expressed as a percentage of control. From left to right, bars show results for controls, 0.5, 5 and 50 $\mu$M R(-)DMS.
Figure 14:
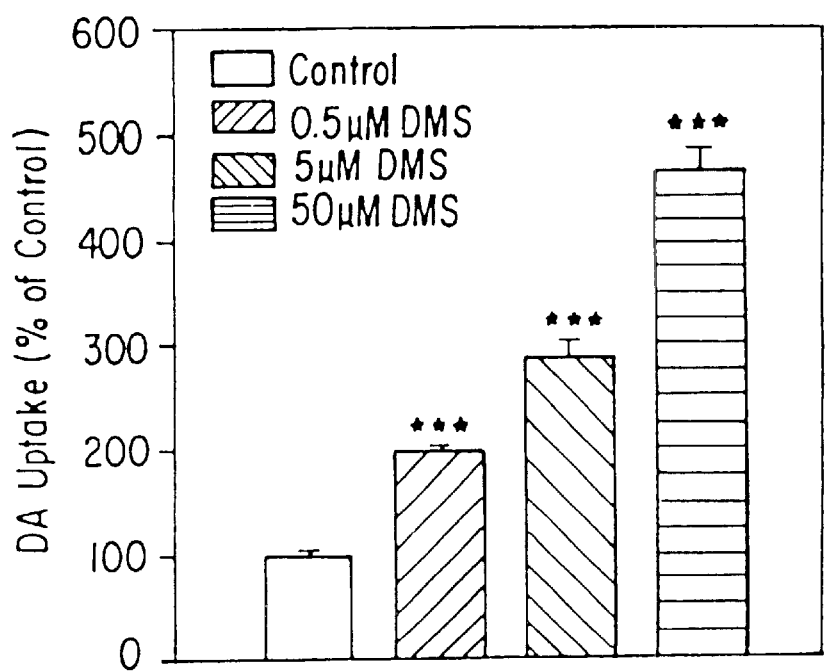
FIG. 14: Effect of R(-)Desmethylselegiline on Dopamine Uptake in Neuronal Cultures. Cell cultures were prepared as described above for FIG. 13 and then tested for uptake of tritiated dopamine. Results for controls and for cells maintained in the presence of 0.5 $\mu$M, 5 $\mu$M and 50 $\mu$M desmethylselegiline are shown from left to right in the figure.

Using the glutamate receptor dependent model of neuron death, an even more potent protection of dopaminergic neurons was provided when desmethylselegiline was used in place of selegiline. Even at the lowest dose tested (0.5 μM), desmethylselegiline caused a significant reduction in the loss of TH positive neurons (FIG. 13) and a significant increase in dopamine uptake (FIG. 14) relative to control cultures in which medium was used without supplementation with either selegiline or desmethylselegiline.

Figure 15:
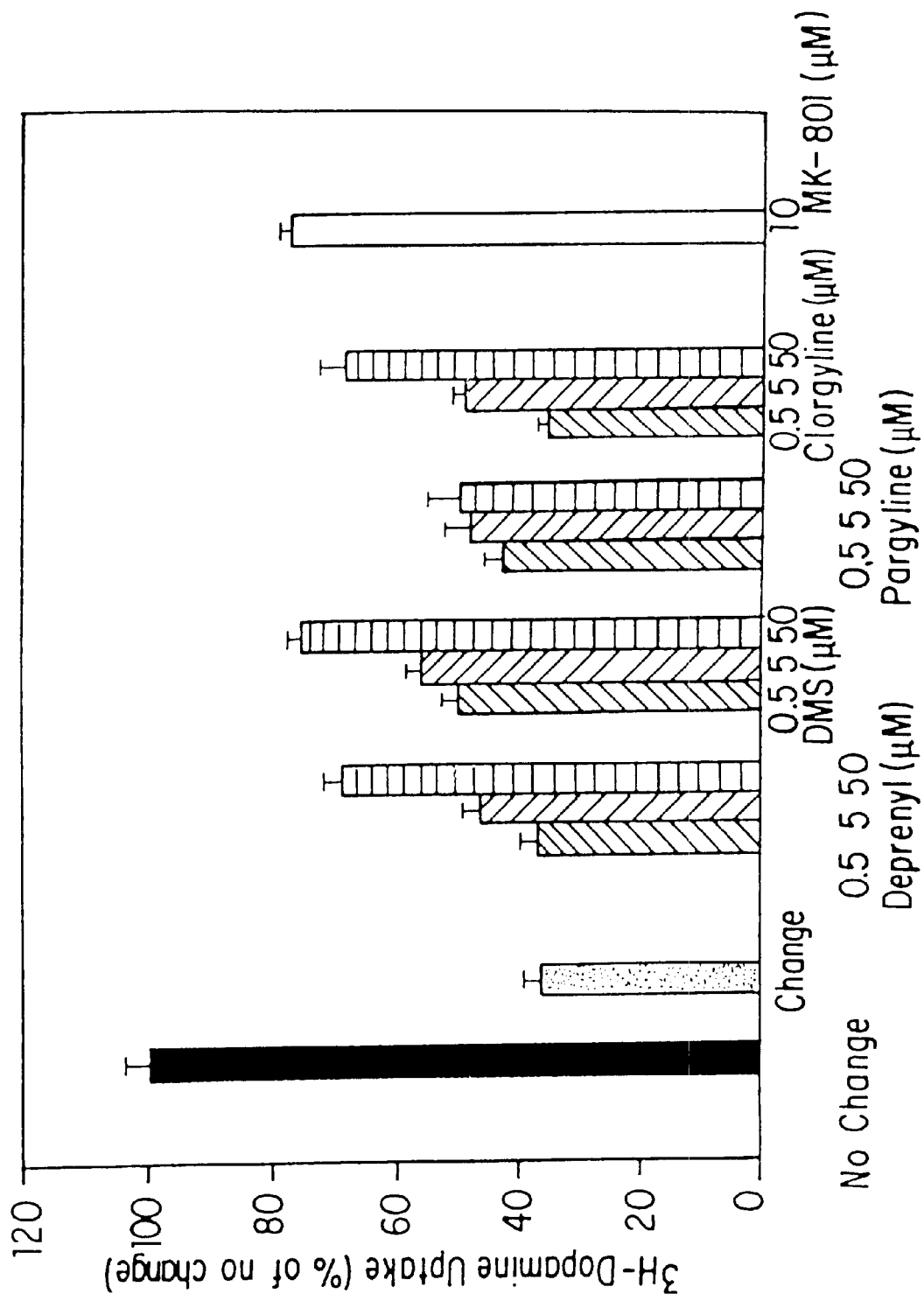
FIG. 15: Comparison of Dopamine Uptake in Mesencephalic Cells Incubated in the Presence of Different Monoamine Oxidase Inhibitors. Rat embryonic mesencephalic cells were prepared as described for FIGS. 11–14 and incubated in the presence of a variety of monoamine oxidase inhibitors. The inhibitors examined were selegiline; R(-) desmethylselegiline; pargyline; and clorgyline, all at concentrations of 0.5, 5 and 50 $\mu$M. In addition, cells were incubated in the presence of the glutamate receptor blocker MK-801 at a concentration of 10 $\mu$M. Cultures were tested for uptake of tritiated dopamine.

D. Comparison With Other MAO Inhibitors. Using the glutamate receptor dependent model of neurotoxicity, the effects of selegiline and desmethylselegiline were compared with two other MAO inhibitors, pargyline and clorgyline (FIG. 15). In agreement with previous results, measurement of dopamine uptake indicated neuron protection by 50 μM deprenyl and 5 and 50 μM desmethylselegiline. Pargyline did not appear to offer any protection at the concentrations used, while clorgyline protected at 50 μM. As expected, protection was also obtained by the NMDA receptor blocker MK-801 (10 μM).

E. Effect of DMS Enantiomers on $^3$H-Dopamine Uptake

The data summarized in Table 4 suggests that both (R-)DMS and S(+)DMS are effective as neuroprotectants in mesencephalic dopamine-containing neurons in culture.

TABLE 4

Effect of DMS Enantiomers on Dopamine Uptake

| Treatment | $^3$H-Dopamine uptake as a percentage + SEM |
|---|---|
| Control | 100 ± 14.14% |
| R(-)DMS (10 μM) | 140.82 ± 26.20% |
| S(+)DMS (10 μM) | 234 ± 38.36% |

These results were obtained using the medium change model of cell death. Compared to untreated control cells, there was 40% and 134% more axonal growth and terminal axonal survival after treatment with R(-)DMS and S(+)DMS, respectively. In this study, S(+)DMS showed greater potency as a neuroprotectant than R(-)DMS.

Example 7

Comparison of the Neuroprotective Effect of R(-)DMS and S(+)DMS

Figure 16:
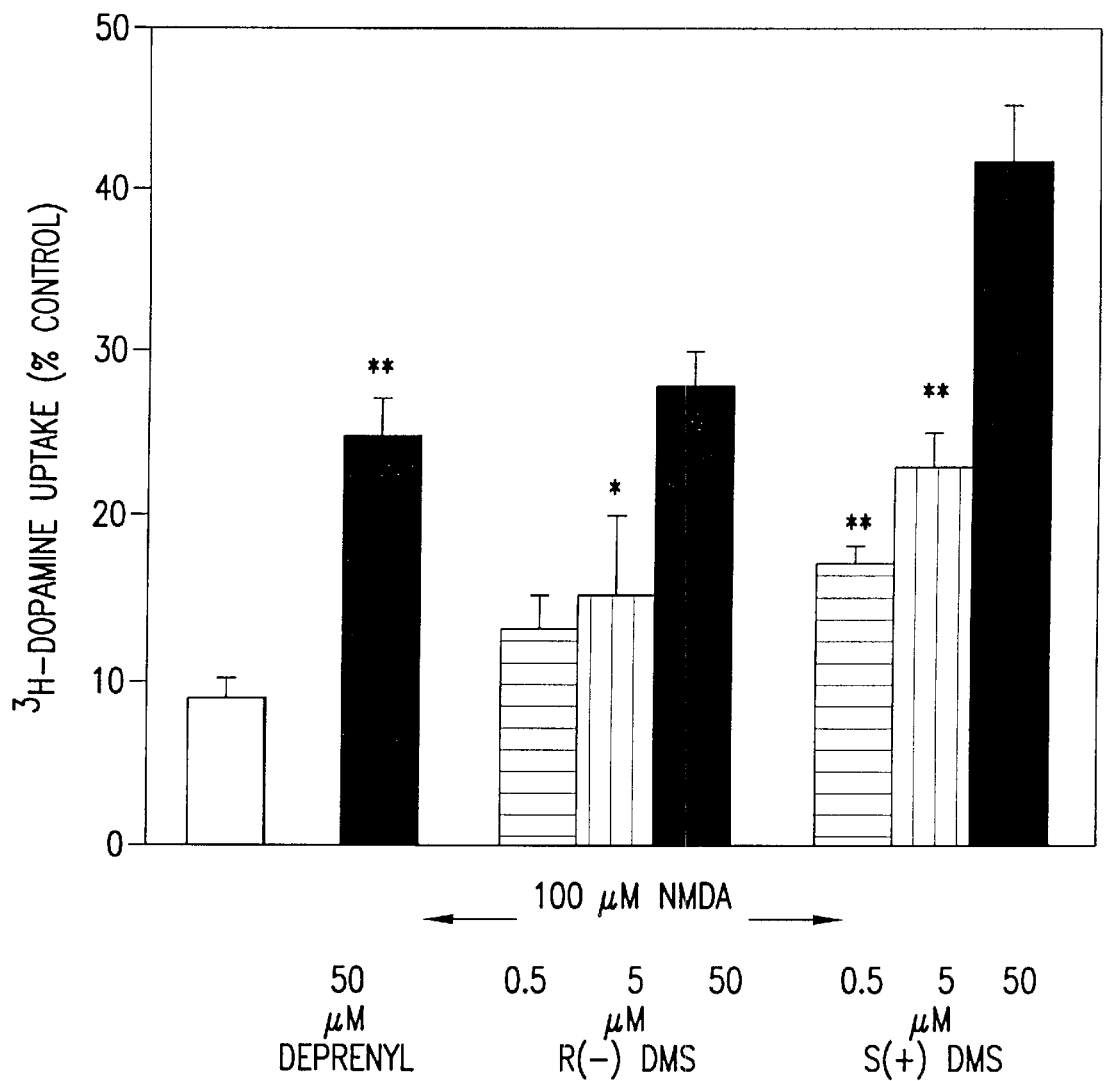
FIG. 16: Relative Effectiveness of R(-) and S(+)DMS in Maintaining [$^3$H]-Dopamine Uptake by Cultured Mesencephalic Cells (NMDA Model). Preparations of R(-) and S(+)DMS were assayed for their effect on [$^3$H]-dopamine uptake by cultured rat mesencephalic cells exposed to the toxin N-methyl-D-aspartate (NMDA). Results were expressed as a percentage of the uptake seen in control cultures not exposed to NMDA and are shown in FIG. 16. From the left, the bars represent: cells incubated with medium alone; medium +5 $\mu$M deprenyl; medium +0.5 $\mu$M R(-)DMS; medium +5 $\mu$M R(-)DMS; medium +50 $\mu$M R(-)DMS; medium +0.5 $\mu$M S(+)DMS; medium +5 $\mu$M S(+)DMS; and medium +50 $\mu$M S(+)DMS. All of the cell cultures shown in the figure were exposed to 100 $\mu$M NMDA. Statistical significance was determined by ANOVA followed by Dunnett's test. One star above a bar indicates a percentage uptake that differs significantly from control uptake at the 0.05 confidence level. Two stars indicate a result that differs at the 0.01 confidence level.
Figure 17:
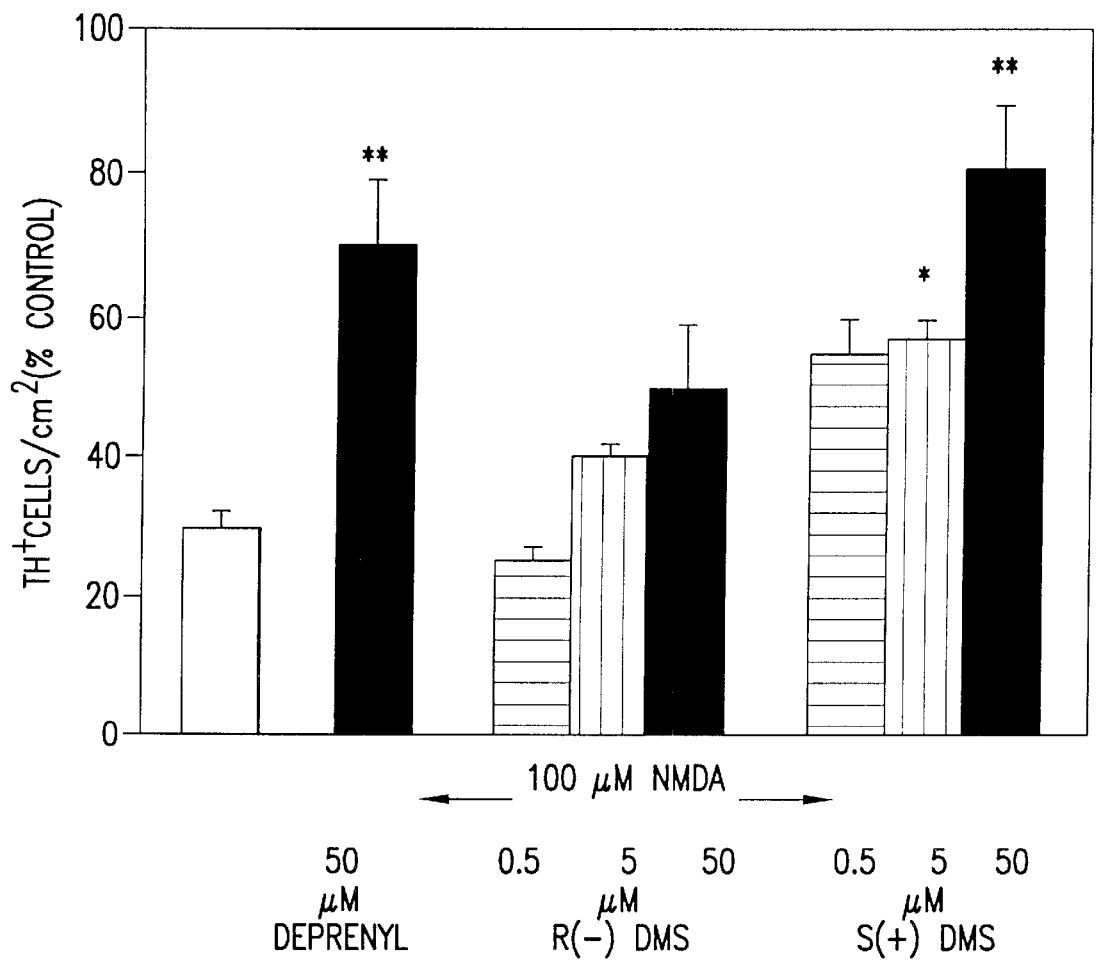
FIG. 17: Relative Effectiveness of R(-) and S(+)DMS on Survival of Cultured Mesencephalic Cells (NMDA Model). Rat mesencephalic cell cultures were exposed to 100 $\mu$M NMDA and incubated as described above in connection with FIG. 16. The effect of DMS enantiomers on the survival TH positive cells is shown in FIG. 17. The bars are in the same order as for FIG. 16 and results are expressed as a percentage of control. One star indicates $p<0.05$ and two stars indicates $p<0.01$ when results are compared to those obtained for cells exposed to NMDA and then incubated in unsupplemented medium.

The neuroprotective effect of R(-)DMS and S(+)DMS on cultured rat mesencephalic cells was examined using two models of neuronal cell death. In the first model, cells were exposed to 100 μM N-methyl-D-aspartate (NMDA), an agent which causes cell death by binding to glutamate receptors. Cells exposed to NMDA were incubated in the presence of either medium alone; medium supplemented with 50 μM deprenyl; medium with 0.5, 5, or 50 μM R(-)DMS; or medium containing 0.5, 5 or 50 μM S(+)DMS. The effect of these treatments on [$^3$H]-dopamine uptake and the survival of TH positive cells was determined and results are shown in Tables 5–8 and FIGS. 16 and 17. It can be seen that both forms of DMS had a neuroprotective effect, with S(+)DMS being the most effective treatment to a statistically significant degree as determined by tritiated dopamine uptake. Experiments examining the neuroprotective effect of DMS enantiomers were also performed using the medium change model of cell death described previously (see Example 6). As can be seen in Tables 9–12, both the R(-) and S(+) enantiomers significantly enhanced [$^3$1H]-dopamine uptake and the survival of TH positive cells. In this model, the relative potency of both enantiomers appears to be equal to treatment with 50 μM selegiline.

TABLE 5

R(-)DMS: Dopamine Uptake After 100 μM NMDA Exposure

|  | Control | R(-)DMS (0.5 μM) | | R(-)DMS (5.0 μM) | | R(-) DMS (50 μM) | | Deprenyl (50 μM) | |
|---|---|---|---|---|---|---|---|---|---|
|  | counts/min | counts/min | % control | counts/min | % control | counts/min | % control | counts/min | % control |
|  | 6013 | 9385 | 138.9 | 13509 | 199.9 | 23090 | 341.8 | 18479 | 273.5 |
|  | 6558 | 8976 | 132.9 | 11471 | 169.8 | 21530 | 318.7 | 16958 | 251.0 |
|  | 7462 | 9028 | 133.6 | 13786 | 204.0 | 17520 | 259.3 | 17550 | 259.8 |
|  | 6432 | 8133 | 120.4 | 10229 | 151.4 | 22963 | 339.9 | 18572 | 274.9 |
|  | 7317 | 11304 | 167.3 | 11014 | 163.0 | 17708 | 262.1 | 15410 | 228.1 |
| Mean | 6756.4 | 9365.2 | 138.6 | 12001.8 | 177.6 | 20562.2 | 304.3 | 17393.8 | 257.4 |
| St. Dev. | 614.3 | 1177.2 | 17.4 | 1569.7 | 23.2 | 2761.0 | 40.9 | 1295.7 | 19.2 |

TABLE 6

S(+)DMS: Dopamine Uptake After 100 AM NMDA Exposure

|  | Control | S(+)DMS (0.5 μM) | | S(+)DMS (5.0 μM) | | S(+)DMS (50 μM) | | Deprenyl (50 μM) | |
|---|---|---|---|---|---|---|---|---|---|
|  | counts/min | counts/min | % control | counts/min | % control | counts/min | % control | counts/min | % control |
|  | 6013 | 12092 | 179.0 | 20313 | 300.6 | 25944 | 384.0 | 18479 | 273.5 |
|  | 6558 | 12269 | 181.6 | 16579 | 245.4 | 28545 | 422.5 | 16958 | 251.0 |

TABLE 6-continued

| | S(+)DMS: Dopamine Uptake After 100 AM NMDA Exposure | | | | | | | |
|---|---|---|---|---|---|---|---|---|
| | Control | S(+)DMS (0.5 μM) | | S(+)DMS (5.0 μM) | | S(+)DMS (50 μM) | | Deprenyl (50 μM) | |
| | counts/min | counts/min | % control | counts/min | % control | counts/min | % control | counts/min | % control |
| | 7462 | 16399 | 242.7 | 15929 | 235.8 | 39042 | 577.9 | 17550 | 259.8 |
| | 6432 | 11435 | 169.2 | 15052 | 222.8 | 33024 | 488.8 | 18572 | 274.9 |
| | 7317 | 11096 | 164.2 | 15535 | 229.9 | 25101 | 371.5 | 15410 | 228.1 |
| Mean | 6756.4 | 12658.2 | 187.4 | 16681.6 | 246.9 | 30331.2 | 448.9 | 17393.8 | 257.4 |
| St. Dev. | 614.3 | 2144.9 | 31.7 | 2105.6 | 31.2 | 5764.6 | 85.3 | 1295.7 | 19.2 |

TABLE 7

| | R(−)DMS: TH Immunochemistry After 100 μM NMDA Exposure | | | | | | | |
|---|---|---|---|---|---|---|---|---|
| | Control | R(−)DMS (0.5 μM) | | R(−)DMS (5.0 μM) | | R(−)DMS (50 μM) | | Deprenyl (50 μM) | |
| | cells/cm² | cells/cm² | % control | cells/cm² | % control | cells/cm² | % control | cells/cm² | % control |
| | 95.0 | 95.0 | 100.9 | 142.5 | 151.3 | 237.5 | 252.2 | 230.0 | 244.2 |
| | 90.0 | 75.0 | 79.6 | 122.5 | 130.1 | 170.0 | 180.5 | 287.5 | 305.3 |
| | 97.5 | 105.0 | 111.5 | 130.0 | 138.1 | 102.5 | 108.8 | 187.5 | 199.1 |
| | | | | 117.5 | 124.8 | 115.0 | 122.1 | 177.5 | 188.5 |
| Mean | 94.17 | 91.67 | 97.3 | 128.13 | 136.1 | 156.25 | 165.9 | 220.63 | 234.3 |
| St. Dev. | 3.8 | 15.3 | 16.2 | 10.9 | 11.5 | 61.6 | 65.4 | 50.1 | 53.2 |

TABLE 8

| | S(+)DMS: TH Immunochemistry After 100 μM NMDA Exposure | | | | | | | |
|---|---|---|---|---|---|---|---|---|
| | Control | S(+)DMS (0.5 μM) | | S(+)DMS (5.0 μM) | | S(+)DMS (50 μM) | | Deprenyl (50 μM) | |
| | cells/cm² | cells/cm² | % control | cells/cm² | % control | cells/cm² | % control | cells/cm² | % control |
| | 95.0 | 127.5 | 135.4 | 192.5 | 204.4 | 297.5 | 315.9 | 230 | 244.2 |
| | 90.0 | 210 | 223.0 | 187.5 | 199.1 | 202.5 | 215.0 | 287.5 | 305.3 |
| | 97.5 | 177.5 | 188.5 | 192.5 | 204.4 | 317.5 | 337.2 | 187.5 | 199.1 |
| | | | | 172.5 | 183.2 | 222.5 | 236.3 | 177.5 | 188.5 |
| Mean | 94.17 | 171.67 | 182.3 | 186.25 | 197.8 | 260 | 276.1 | 220.63 | 234.3 |
| St. Dev. | | 41.6 | 44.1 | 9.5 | 10.1 | 56.1 | 59.5 | 50.1 | 53.2 |

TABLE 9

| | R(−)DMS: Dopamine Uptake, Medium Change Model | | | | | | | |
|---|---|---|---|---|---|---|---|---|
| | Control | R(−)DMS (0.5 μM) | | R(−)DMS (5.0 μM) | | R(−) DMS (50 μM) | | Deprenyl (50 μM) | |
| | counts/min | counts/min | % control | counts/min | % control | counts/min | % control | counts/min | % control |
| | 17880 | 29885 | 142.3 | 32577 | 155.2 | 37440 | 178.3 | 38053 | 181.2 |
| | 21500 | 32002 | 152.4 | 29831 | 142.1 | 39200 | 186.7 | 34130 | 162.6 |
| | 23471 | 29934 | 142.6 | 36370 | 173.2 | 39126 | 186.3 | 36810 | 175.3 |
| | 21134 | 27382 | 130.4 | 30342 | 144.5 | 40013 | 190.6 | 33863 | 161.3 |
| Mean | 20996.25 | 29800.75 | 141.9 | 32280 | 153.7 | 38944.75 | 185.5 | 35714 | 170.1 |
| St. Dev. | 2317.2 | 1890.4 | 9.0 | 2976.0 | 14.2 | 1080.7 | 5.1 | 2050.0 | 9.8 |

TABLE 10

S(+)DMS: Dopamine Uptake, Medium Change Model

|  | Control | R(−)DMS (0.5 μM) | | R(−)DMS (5.0 μM) | | R(−) DMS (50 μM) | | Deprenyl (50 μM) | |
|---|---|---|---|---|---|---|---|---|---|
|  | counts/min | counts/min | % control | counts/min | % control | counts/min | % control | counts/min | % control |
|  | 17880 | 35830 | 170.6 | 35976 | 171.3 | 26002 | 123.8 | 38053 | 181.2 |
|  | 21500 | 32074 | 152.8 | 36476 | 173.7 | 37320 | 177.7 | 34130 | 162.6 |
|  | 23471 | 33042 | 157.4 | 38143 | 181.7 | 30725 | 146.3 | 36810 | 175.3 |
|  | 21134 | 39516 | 188.2 | 40964 | 195.1 | 38020 | 181.1 | 33863 | 161.3 |
| Mean | 20996.25 | 35115.5 | 167.2 | 37889.75 | 180.5 | 33016.75 | 157.3 | 35714 | 170.1 |
| St. Dev. | 2317.2 | 3337.9 | 15.9 | 2249.2 | 10.7 | 5715.7 | 27.2 | 2050.0 | 9.8 |

TABLE 11

R(−)DMS: TH Immunochemistry, Medium Change Model

|  | Control | R(−)DMS (0.5 μM) | | R(−)DMS (5.0 μM) | | R(−)DMS (50 μM) | | Deprenyl (50 μM) | |
|---|---|---|---|---|---|---|---|---|---|
|  | cells/cm² | cells/cm² | % control | cells/cm² | % control | cells/cm² | % control | cells/cm² | % control |
|  | 270.0 | 340.0 | 129.0 | 322.5 | 122.3 | 310.0 | 117.6 | 385.0 | 146.0 |
|  | 237.0 | 310.0 | 117.6 | 342.5 | 129.9 | 442.5 | 167.9 | 327.5 | 124.2 |
|  | 280.0 | 330.0 | 125.2 | 362.5 | 137.5 | 380.0 | 144.1 | 320.0 | 121.4 |
|  | 267.5 | 362.5 |  | 365.0 | 138.5 | 395.0 | 149.8 |  |  |
| Mean | 263.63 | 335.63 | 123.9 | 348.13 | 132.1 | 381.88 | 144.9 | 344.17 | 130.6 |
| St. Dev. | 18.6 | 21.8 | 5.8 | 19.8 | 7.5 | 54.8 | 20.8 | 35.6 | 13.5 |

TABLE 12

S(+)DMS: TH Immunochemistry, Medium Change Model

|  | Control | S(+)DMS (0.5 μM) | | S(+)DMS (5.0 μM) | | S(+)DMS (50 μM) | | Deprenyl (50 μM) | |
|---|---|---|---|---|---|---|---|---|---|
|  | cells/cm² | cells/cm² | % control | cells/cm² | % control | cells/cm² | % control | cells/cm² | % control |
|  | 270.0 | 402.5 | 152.7 | 342.5 | 129.9 | 307.5 | 116.6 | 385.0 | 146.0 |
|  | 237.0 | 330.0 | 125.2 | 357.5 | 135.6 | 250.0 | 94.8 | 327.5 | 124.2 |
|  | 280.0 | 402.5 | 152.7 | 325.0 | 123.3 | 312.5 | 118.5 | 320.0 | 121.4 |
|  | 267.5 | 477.5 |  | 352.5 | 133.7 | 287.5 | 109.1 |  |  |
| Mean | 263.6 | 403.1 | 143.5 | 344.4 | 130.6 | 289.4 | 109.8 | 344.2 | 130.6 |
| St. Dev. | 18.6 | 60.2 | 15.9 | 14.3 | 5.4 | 28.4 | 10.8 | 35.6 | 13.5 |

Example 8

Desmethylselegiline and Ent-Desmethylselegiline as Inhibitors of Dopamine Re-Uptake The biological actions of the brain neurotransmitter dopamine are terminated at the synapse by a high-affinity, sodium and energy-dependent transport system (neuronal reuptake) present within the limiting membrane of the presynaptic dopamine—containing nerve terminal. Inhibition of this transport mechanism would extend the actions of dopamine at the synapse and therefore enhance dopamine synaptic transmission.

A. Method of Testing

The R(−) and S(+) enantiomers of desmethylselegiline (DMS) were tested for their ability to inhibit the dopamine re-uptake system and compared to selegiline. Inhibitory activity in this assay is indicative of agents of value in the treatment of diseases which require enhanced synaptic dopamine activity. Presently this would include Parkinson's disease, Alzheimer's disease and attention deficit hyperactivity disorder (ADHD).

The assay system used was essentially that described by Fang et al. (*Neuropharmacology* 33:763–768 (1994)). An in vitro nerve-terminal preparation (synaptosome preparation) was obtained form fresh rat neostriatal brain tissue. Transport by dopamine nerve-terminals was estimated by measuring the uptake of tritiated dopamine.

B. Results

As seen in the data presented in Table 13, selegiline, R(−)DMS and S(+)DMS all inhibited dopamine re-uptake by dopamine-containing nerve terminals. Selegiline and R(−) DMS were approximately equipotent. In contrast, S(+)DMS was 4–5 times more potent than either selegiline or R(−)DMS.

TABLE 13

3H-Dopamine Uptake By Rat Neostriatal Brain Tissue

| Agent | Concentration | % Reduction x ± SEM |
|---|---|---|
| Dopamine | 1 μM | 52.0 ± 4.9 |
| | 10 μM | 80.9 ± 0.4 |
| Selegiline | 100 μM | 7.0 ± 3.6 |
| | 1 μM | 13.9 ± 4.7 |
| | 10 μM | 16.3 ± 3.8 |
| | 100 μM | 59.8 ± 1.0 |
| R(−)DMS | 100 μM | 11.5 ± 1.0 |
| | 1 μM | 10.7 ± 2.8 |
| | 10 μM | 20.1 ± 3.1 |
| | 100 μM | 51.3 ± 2.6 |
| S(+)DMS | 100 μM | 15.3 ± 7.7 |
| | 1 μM | 24.1 ± 11.7 |
| | 10 μM | 47.0 ± 3.1 |
| | 100 μM | 76.9 ± 1.8 |

Figure 18:
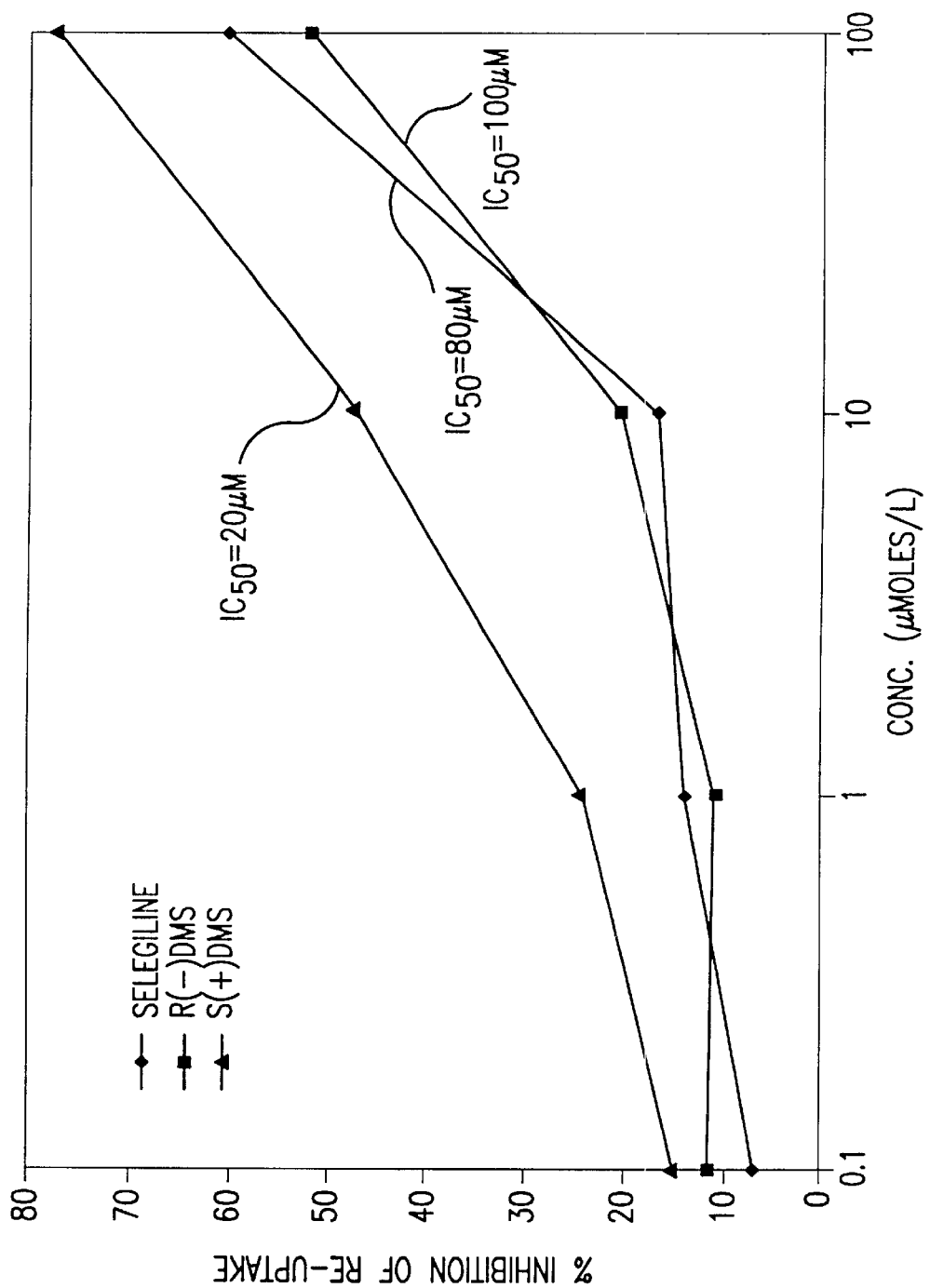
FIG. 18: Inhibition of Neuronal Dopamine Re-Uptake by Deprenyl and the Two Enantiomers of Desmethylselegiline. An in vitro nerve terminal preparation (synaptosome preparation) was prepared using fresh rat neostriatal tissue. This was examined for its ability to take up tritiated dopamine in buffer alone or in buffer supplemented with various concentrations of selegiline, R(-)desmethylselegiline or S(+)desmethylselegiline. Uptake in the presence of each MAO inhibitor, expressed as a percent inhibition vs. log concentration of inhibitor is shown in FIG. 18. As indicated, the plot was used to determine the $IC_{50}$ for each test agent.

Relative potency can be expressed in terms of the concentration required to inhibit dopamine re-uptake by 50% ($IC_{50}$). The ICS values were determined graphically (see FIG. 18) and are shown below in Table 14.

TABLE 14

Concentrations Needed to Inhibit Dopamine Uptake by 50

| Agent | $IC_{50}$ | Relative Potency |
|---|---|---|
| Selegiline | ≈80 μM | 1 |
| R(−)DMS | ≈100 μM | 0.8 |
| S(+)DMS | ≈20 μM | 4 |

Figure 19:
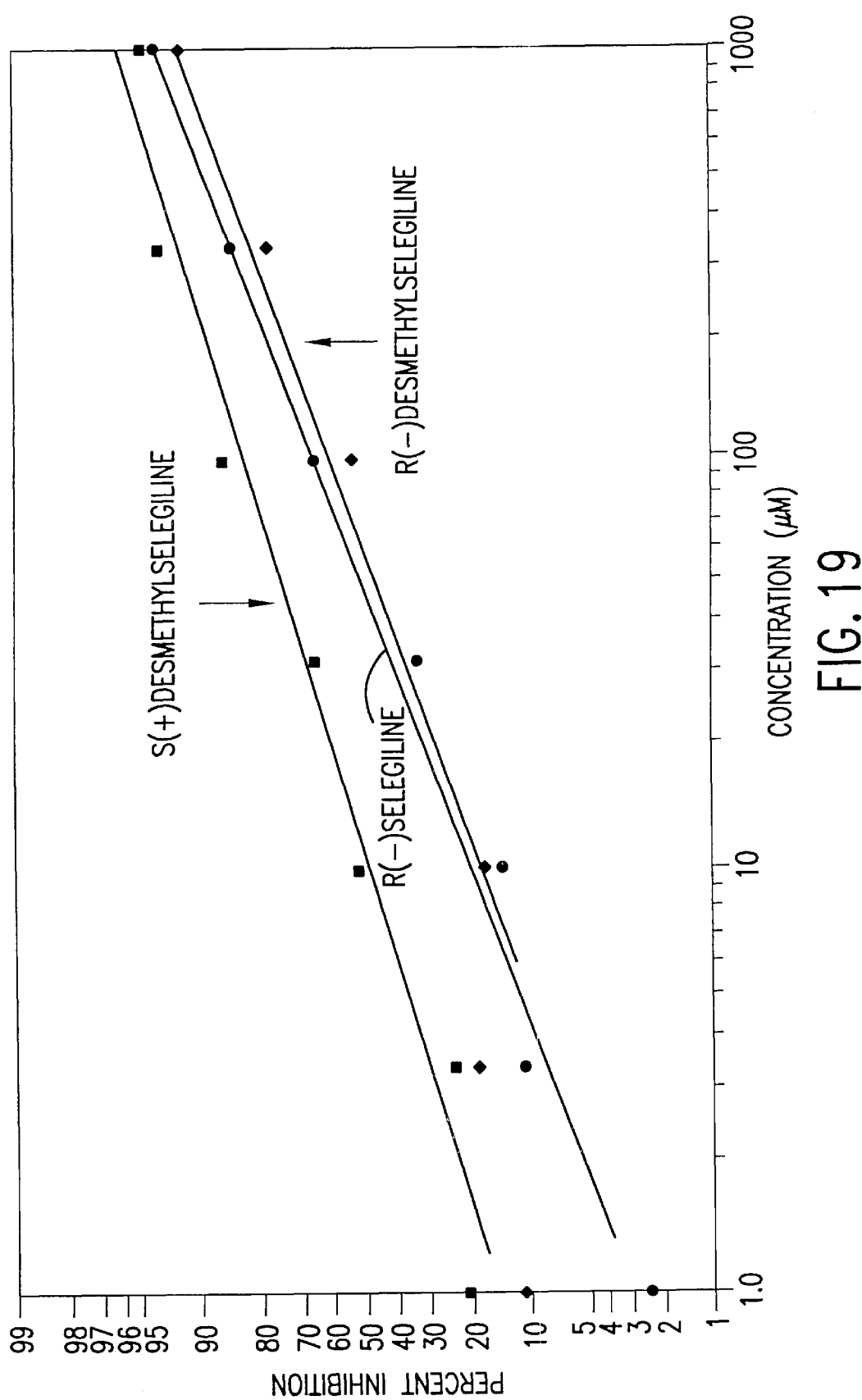
FIG. 19: Determination of $IC_{50}$ Values for Inhibition of Dopamine Re-Uptake. The experiment of FIG. 18 was repeated in a concentration range designed to more accurately provide an $IC_{50}$ value and results are shown in FIG. 19. Using the log C vs. probit graphs, as shown in the figure, the $IC_{50}$ for S(+)DMS was determined to be about 11 $\mu$M; for selegiline, about 46 $\mu$M; and for R(-)DMS about 54 $\mu$M.

The experiment described above was repeated in a concentration range designed to more accurately describe $IC_{50}$ values and results are shown in FIG. 19. $ID_{50}$ values determined based upon the graph are shown in Table 15.

TABLE 15

Concentrations Needed to Inhibit Dopamine Uptake by 50%

| Compound | $ID_{50}$ | Potency Relative to selegiline |
|---|---|---|
| S(+)DMS | 11 μM | 4.2 |
| selegiline | 46 μM | 1 |
| R(−)DMS | 54 μM | 1.2 |

C. Conclusions

The results demonstrate that, at the appropriate concentration, selegiline and each of the enantiomers of DMS inhibit transport of released dopamine at the neuronal synapse and enhance the relative activity of this neurotransmitter at the synapse. In this regard, S(+)DMS is more potent than selegiline which, in turn, is more potent than R(−)DMS. Of the agents tested, S(+)DMS is the most preferred with regard to the treatment of hypodopaminergic conditions such as ADHD.

Example 9

Actions of the R(−) and S(+)enantiomers of Desmethylselegiline (DMS) on Human Platelet MAO-B and Guinea Pig Brain MAO-B and MAO-A Activity Human platelet MAO is comprised exclusively of the type -B isoform of the enzyme. In the present study, the in vitro and in vivo inhibition of this enzyme by the two enantiomers of DMS was determined and compared with inhibition due to selegiline. The present study also examined the two enantiomers of DMS for inhibitory activity with respect to the MAO-A and MAO-B in guinea pig hippocampal tissue. Guinea pig brain tissue is an excellent animal model for studying brain dopamine metabolism, the enzyme kinetics of the multiple forms of MAO and the inhibitory properties of novel agents that interact with these enzymes. The multiple forms of MAO in this animal species show similar kinetic properties to those found in human brain tissue. Finally, the test agents were administered to guinea pigs and the extent to which they might act as inhibitors of brain MAO in vivo was assessed.

A. Method of Testing

In vitro: The test system utilized the in vitro conversion of specific substrates of MAO-A ($^{14}$C-serotonin) and MAO-B ($^{14}$C-phenylethylamine) by human platelets and/or guinea pig hippocampal homogenates. The rate of conversion of each substrate was measured in the presence of S(+)DMS, R(−)DMS or selegiline and compared to the isozyme activity in the absence of these agents. A percent inhibition was calculated from these values. Potency was evaluated by comparing the concentration of each agent which caused a 50% inhibition ($IC_{50}$ value).

In vivo: R(−)DMS, S(+)DMS or selegiline was administered in vivo subcutaneously (sc), once a day for 5 days prior to sacrifice, preparation of enzyme hippocampal homogenates, and the in vitro assay of MAO-A and MAO-B activity. These experiments were performed to demonstrate that the DMS enantiomers were capable of entering brain tissue and inhibiting MAO activity.

B. Results

MAO-B Inhibitory Activity In Vitro

Results for MAO-B inhibition are shown in Tables 16 and 17. $IC_{50}$ values for MAO-B inhibition and potency as compared to selegiline is shown in Table 18.

TABLE 16

MAO-B Inhibition in Human Platelets

| Agent | Concentration | % Inhibition x ± SEM |
|---|---|---|
| Selegiline | 0.3 nM | 8.3 ± 3.4 |
| | 5 nM | 50.3 ± 8.7 |
| | 10 nM | 69.0 ± 5.5 |
| | 30 nM | 91.0 ± 1.4 |
| | 100 nM | 96.0 ± 1.6 |
| | 300 nM | 96.0 ± 1.6 |
| | 1 μM | 96.6 ± 1.6 |
| R(−)DMS | 100 nM | 14.3 ± 3.6 |
| | 300 nM | 42.1 ± 4.0 |
| | 1 μM | 76.9 ± 1.47 |
| | 3 μM | 94.4 ± 1.4 |
| | 10 μM | 95.8 ± 1.4 |
| | 3 μM | 95.7 ± 2.3 |
| S(+)DMS | 300 nM | 6.4 ± 2.8 |
| | 1 μM | 11.1 ± 1.0 |
| | 3 μM | 26.6 ± 1.9 |
| | 10 μM | 42.3 ± 2.3 |
| | 30 μM | 68.2 ± 2.34 |
| | 100 μM | 83.7 ± 0.77 |
| | 1 mM | 94.2 ± 1.36 |

TABLE 17

MAO-B Inhibition in Guinea Pig Hippocampus

| Agent | Concentration | % inhibition x ± SEM |
|---|---|---|
| Selegiline | 0.3 nM | 28.3 ± 8.7 |
|  | 5 nM | 81.2 ± 2.6 |
|  | 10 nM | 95.6 ± 1.3 |
|  | 30 nM | 98.5 ± 0.5 |
|  | 100 nM | 98.8 ± 0.5 |
|  | 300 nM | 98.8 ± 0.5 |
|  | 1 pM | 99.1 ± 0.45 |
| R(−)DMS | 100 nM | 59.4 ± 9.6 |
|  | 300 nM | 86.2 ± 4.7 |
|  | 1 µM | 98.2 ± 0.7 |
|  | 3 µM | 98.4 ± 0.95 |
|  | 10 µM | 99.1 ± 0.45 |
|  | 30 µM | 99.3 ± 0.40 |
| S(+)DMS | 300 nM | 18.7 ± 2.1 |
|  | 1 µM | 44.4 ± 6.4 |
|  | 3 µM | 77.1 ± 6.0 |
|  | 10 µM | 94.2 ± 1.9 |
|  | 30 µM | 98.3 ± 0.6 |
|  | 100 µM | 99.3 ± 0.2 |
|  | 1 mM | 99.9 ± 0.1 |

TABLE 18

IC50 Values for the Inhibition of MAO-B

| Treatment | Human Platelets | Guinea Pig Hippocampal Cortex |
|---|---|---|
| Selegiline | 5 nM (1) | 1 nM (1) |
| R(−)DMS | 400 nM (80) | 60 nM (60) |
| S(+)DMS | 1400 nM (2800) | 1200 nM (1200) |

As observed, R(−)DMS was 20–35 times more potent than S(+)DMS as an MAO-B inhibitor and both enantiomers were less potent than selegiline.

MAO-A Inhibitory Activity In Vitro

Results obtained from experiments examining the inhibition of MAO-A in guinea pig hippocampus are summarized in Table 19. The $IC_{50}$ values for the two enantiomers of DMS and for selegiline are shown in Table 20.

TABLE 19

MAO-A Inhibition in Guinea Pig Hippocampus

| Agent | Concentration | % Inhibition x ± SEM |
|---|---|---|
| Selegiline | 300 nM | 11.95 ± 2.4 |
|  | 1 µM | 22.1 ± 1.2 |
|  | 3 µM | 53.5 ± 2.7 |
|  | 10 µM | 91.2 ± 1.16 |
|  | 100 µM | 98.1 ± 1.4 |
|  | 1 mM | 99.8 ± 0.2 |
| R(−)DMS | 300 nM | 4.8 ± 2.1 |
|  | 1 µM | 4.2 ± 1.5 |
|  | 3 µM | 10.5 ± 2.0 |
|  | 10 µM | 19.0 ± 1.3 |
|  | 100 µM | 64.2 ± 1.5 |
|  | 1 mM | 96.5 ± 1.2 |
| S(+)DMS | 1 µM | 3.3 ± 1.5 |
|  | 3 µM | 4.3 ± 1.0 |
|  | 10 µM | 10.5 ± 1.47 |
|  | 100 µM | 48.4 ± 1.8 |
|  | 1 mM | 92.7 ± 2.5 |
|  | 10 mM | 99.6 ± 0.35 |

TABLE 20

$IC_{50}$ Values for the Inhibition of MAO-A

| Treatment | $IC_{50}$ for MAO-A in Guinea Pig Hippocampal Cortex |
|---|---|
| Selegiline | 2.5 µM (1) |
| R(−)DMS | 50.0 µM (20) |
| S(+)DMS | 100.0 µM (40) |

( ) = reduction in potency compared to selegiline

R(−)DMS was twice as potent as S(+)DMS as an MAO-A inhibitor and both were 20–40 times less potent than selegiline. Moreover, each of these agents were 2–3 orders of magnitude, i.e., 100 to 1000 times, less potent as inhibitors of MAO-A than inhibitors of MAO-B in hippocampal brain tissue. Therefore, selegiline and each enantiomer of DMS can be classified as selective MAO-B inhibitors in brain tissue.

Results of In Vivo Experiments

Figure 20:
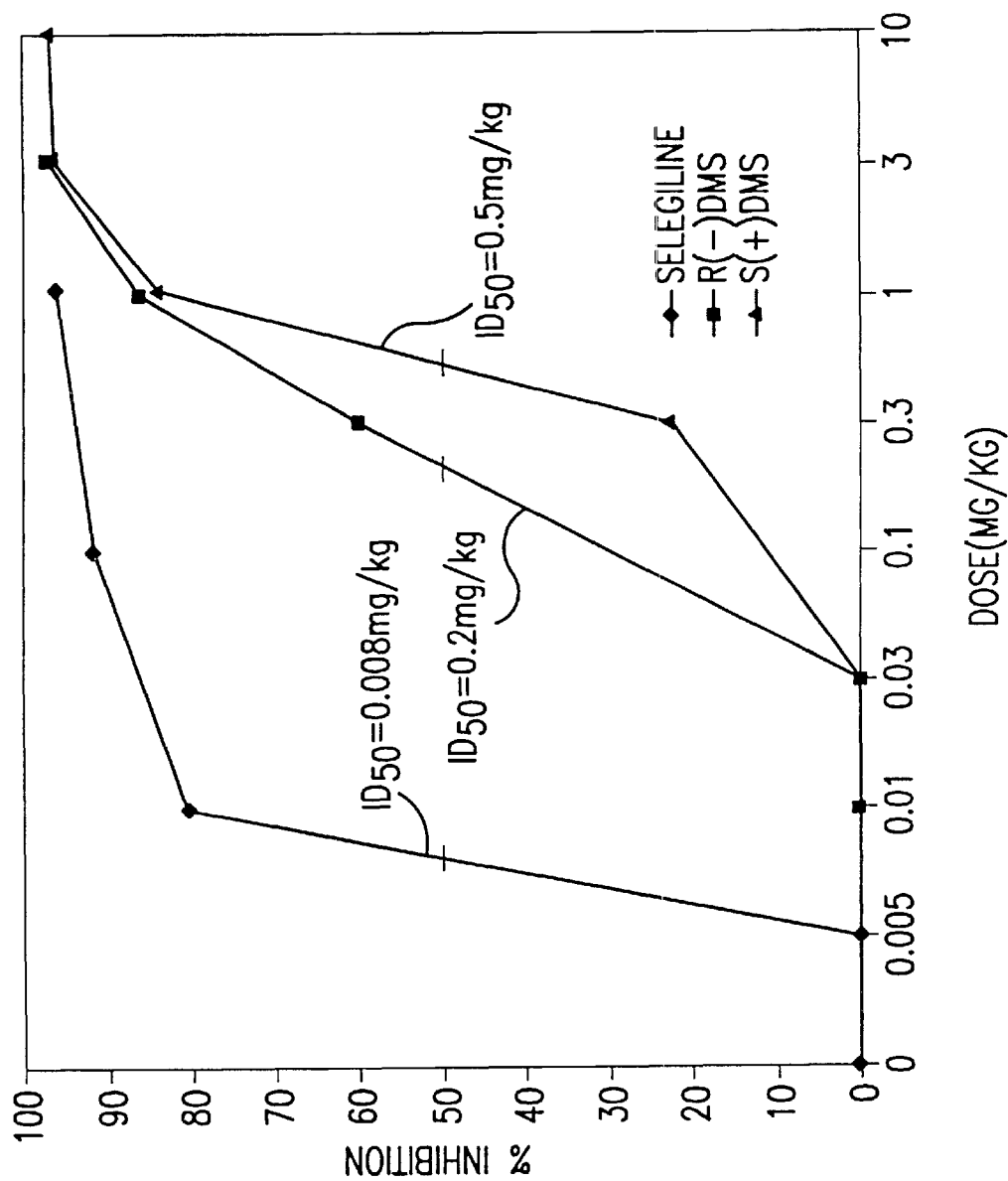
FIG. 20: In Vivo MAO-B Inhibition in Guinea Pig Hippocampus. Various doses of selegiline, R(-)desmethylselegiline, and S(+)desmethylselegiline were administered daily into guinea pigs for a period of 5 days. Animals were then sacrificed and the MAO-B activity in the hippocampus portion of the brain was determined. Results were expressed as a percent inhibition relative to hippocampus MAO-B activity in control animals and are shown in FIG. 20. The plots were used to estimate the $ID_{50}$ dosage for each agent. The $ID_{50}$ for selegiline was about 0.008 mg/kg; and for R(−)DMS, it was about 0.2 mg/kg; and for S(+) DMS, it was about 0.5 mg/kg.

Each enantiomer of DMS was administered in vivo by subcutaneous injection once a day for five consecutive days, and inhibition of brain MAO-B activity was then determined. In preliminary studies, selegiline was found to have an $ID_{50}$ of 0.03 mg/kg and both R(−)DMS and S(+)DMS were determined to be about 10 times less potent. More recent studies, performed on a larger group of animals, indicates that R(−)DMS is actually about 25 times less potent than selegiline as an inhibitor of MAO-B and that S(+)DMS is about 50 times. less potent. Results are shown in FIG. 20 and $ID_{50}$ values are summarized in Table 21.

TABLE 21

$ID_{50}$ Values for Brain MAO-B Following 5 Days of Administration

| Treatment | $ID_{50}$ for MAO-B in Guinea Pig Hippocampal Cortex |
|---|---|
| Selegiline | 0.008 mg/kg |
| R(−)DMS | 0.20 mg/kg |
| S(+)DMS | 0.50 mg/kg |

This experiment demonstrates that the enantiomers of DMS penetrate the blood brain-barrier and inhibit brain MAO-B after in vivo administration. It also demonstrates that the potency differences as an MAO-B inhibitor observed in vitro between each of the DMS enantiomers and selegiline are substantially reduced under in vivo conditions.

In experiments examining the effect of 5 s.c. treatments on MAO-A activity in guinea pig cortex (hippocampus), it was found that selegiline administration at a dose of 1.0 mg/kg resulted in a 36.1% inhibition of activity. R(−)DMS resulted in an inhibition of 29.8% when administered at a dose of 3.0 mg/kg. S(+)DMS administration did not cause any observable inhibition at the highest dose tested (10 mg/kg) indicating that it has significantly less cross reactivity potential.

C. Conclusions

In vitro, R(−)DMS and S(+)DMS both exhibit activity as MAO-B and MAO-A inhibitors. Each enantiomer was selective for MAO-B. S(+)DMS was less potent than R(−)DMS and both enantiomers of DMS were less potent than selegiline in inhibiting both MAO-A and MAO-B.

In vivo, both enantiomers demonstrated activity in inhibiting MAO-B, indicating that these enantiomers are able to pass through the blood-brain barrier. The ability of these agents to inhibit MAO-B suggests that these agents may be of value as therapeutics for hypodopaminergic diseases such as ADHD and dementia.

Example 10

In Vivo Neuroprotection by the Enantiomers of Desmethylselegiline

The ability of the enantiomers of DMS to prevent neurological deterioration was examined by administering the agents to the wobbler mouse, an animal model of motor neuron diseases, particularly amyotrophic lateral sclerosis (ALS). Wobbler mice exhibit progressively worsening forelimb weakness, gait disturbances, and flexion contractions of the forelimb muscles.

A. Test Method

A 0.1 mg/kg dose of R(−)DMS, S(+)DMS or placebo was administered to wobbler mice by daily intra-peritoneal injection for a period of 30 days in a randomized, double-blind study. At the end of this time mice were examined for grip strength, running time, resting locomotive activity and graded for semi-quantitative paw posture abnormalities, and semi-quantitative walking abnormalities. The investigators who prepared and administered the test drugs to the animals were different than those who analyzed behavioral changes.

Assays and grading were performed essentially as described in Mitsumoto et al., Ann. Neurol. 36:142–148 (1994). Grip strength of the front paws of a mouse was determined by allowing the animal to grasp a wire with both paws. The wire was connected to a gram dynamometer and traction is applied to the tail of the mouse until the animal is forced to release the wire. The reading on the dynamometer at the point of release is taken as a measure of grip strength.

Running time is defined as the shortest time necessary to traverse a specified distance, e.g. 2.5 feet and the best time of several trials is recorded.

Paw posture abnormalities are graded on a scale based upon the degree of contraction and walking abnormalities are graded on a scale ranging from normal walking to an inability to support the body using the paws.

Locomotive activity is determined by transferring animals to an examination area in which the floor is covered with a square grid. Activity is measured by the number of squares traversed by a mouse in a set time interval, e.g., 9 minutes.

B. Results

At the beginning of the study, none of the groups were different in any variables, indicating that the three groups were comparative at the baseline. Weight gain was identical in all three groups, suggesting that no major side effects occurred in any animals. Table 22 summarizes differences that were observed in the mean grip strength of the test animals:

TABLE 22

Mean Grip Strength in Wobbler Mice Treated with R(−) or S(+)DMS

| Treatment | N | Grip Strength (gm) |
| --- | --- | --- |
| Control (placebo) | 10 | 9 (0–15) |
| R(−)DMS | 9 | 20 (0–63) |
| S(+)DMS | 9 | 14 (7–20) |

N = number of animals analyzed

Grip strength dropped markedly at the end of the first week in all animals. At the end of the study, grip strength was the least in control animals. The variability in grip strength in the treated animal groups prevented a meaningful statistical analysis of this data, however, at a dose of 0.1 mg/kg, the mean grip strength measured in the DMS-treated animals was greater than for the controls. These results suggest that the dose may have been too low, and that a higher dose study should be performed.

Running time, resting locomotive activity, semiquantitative paw posture abnormality grading, and semi-quantitative walking abnormality grading were also tested. None of these tests, however, showed any difference among the three groups tested.

Example 11

Immune System Restoration by R(−)DMS and S(+)DMS

There is an age-related decline in immunological function that occurs in animals and humans which makes older individuals more susceptible to infectious disease and cancer. U.S. Pat. Nos. 5,276,057 and 5,387,615 suggest that selegiline is useful in the treatment of immune system dysfunction. The present experiments were undertaken to determine whether R(−)DMS and S(+) are also useful in the treatment of such dysfunction. It should be recognized that an ability to bolster a patient's normal immunological defenses would be beneficial in the treatment of a wide variety of acute and chronic diseases including cancer, AIDS, and both bacterial and viral infections.

A. Test Procedure

The present experiments utilized a rat model to examine the ability of R(−)DMS and S(+)DMS to restore immunological function. Rats were divided into the following experimental groups:

1) young rats (3 months old, no treatment);
2) old rats (18–20 months old, no treatment);
3) old rats injected with saline;
4) old rats treated with selegiline at a dosage of 0.25 mg/kg body weight;
5) old rats treated with selegiline at a dosage of 1.0 mg/kg body weight;
6) old rats treated with R(−)DMS at a dosage of 0.025 mg/kg body weight;
7) old rats treated with R(−)DMS at a dosage of 0.25 mg/kg body weight;
8) old rats treated with R(−)DMS at a dosage of 1.0 mg/kg body weight;
9) old rats treated with S(+)DMS at a dosage of 1.0 mg/kg body weight.

Rats were administered saline or test agent ip, daily for 60 days. They were then maintained for an additional "wash out" period of 10 days during which time no treatment was given. At the end of this time, animals were sacrificed and their spleens were removed. The spleen cells were then assayed for a variety of factors which are indicative of immune system function. Specifically, standard tests were employed to determine the following:

1) in vitro production of γ-interferon by concanavalin A-stimulated spleen cells;
2) in vitro concanavalin A-induced production of interleukin-2;
3) percentage of IgM positive spleen cells (IgM is a marker of B lymphocytes;
4) percentage of CD5 positive spleen cells (CD5 is a marker of T lymphocytes).

B. Results

The effect of administration of selegiline, R(−)DMS and S(+)DMS on concanavalin A-induced interferon production by rat spleen cells is shown in Tables 23 and 24. Table 23 shows that there is a sharp decline in cellular interferon production that occurs with age. Administration of selegiline, R(−)DMS and S(+)DMS all led to a restoration of γ-interferon levels with the most dramatic increases occurring at dosages of 1.0 mg/kg body weight.

TABLE 23

Effect of Age on T Cell Function*

| Groups | IL-2 | | IFN-γ | |
|---|---|---|---|---|
| | U/ml | std. error | U/ml | std. error |
| young | 59.4 | 18.27 | 12297 | 6447 |
| old | 19.6 | 7.52 | 338 | 135 |

*T cell activities were assessed after stimulation of rat spleen cells with concanavalin A. TH, cytokines, IL-2 and IFN-y were measured. young vs. old, p = 0.0004

TABLE 24

Mean and % control IL-2 and IFN g

| Groups | IL-2 U/ml | | IFN-γ U/ml | |
|---|---|---|---|---|
| | mean | % control | mean | % control |
| control* | 19.64 | 100 | 351 | 100 |
| control | 41.22 | 210 | 339 | 96 |
| R(−)DMS | 55.17 | 281 | 573 | 163 |
| R(−)DMS | 64.54 | 329 | 516 | 147 |
| R(−)DMS | 43.7 | 223 | 2728 | 777 |
| S(+)DMS | 57.12 | 291 | 918 | 261 |
| Sel 0.25 | 109.6 | 558 | 795 | 226 |
| Sel. 1.0 | 73.78 | 376 | 1934 | 550 |

*Old rats (22 months old) with no treatment

Table 24 shows the extent to which R(−)DMS, S(+)DMS and selegiline are capable of restoring γ-interferon production in the spleen cells of old rats. Interferon-y is a cytokine associated with T cells that inhibit viral replication and regulate a variety of immunological functions. It influences the class of antibodies produced by B-cells, up-regulates class I and class II MHC complex antigens and increases the efficiency of macrophage-mediated killing of intracellular parasites.

Histological immunofluorescence studies show a dramatic loss of innervation in rat spleens with age. When rats are treated with R(−)DMS, there is a significant increase in innervation in the spleens of animals and this increase occurs in a dose-response manner. S(+) DMS did not show any effect on histological examination, despite a modest increase in interferon-γ production. IL-2 production was not enhanced by treatment with R(−)DMS or S(+)DMS, suggesting that the effects of these agents may be limited to IFN-γ production.

C. Conclusions

The results obtained with respect to histological examination, the production of interferon, and the percentage of IgM positive spleen cells support the conclusion that the DMS enantiomers are capable of at least partially restoring the age-dependent loss of immune system function. The results observed with respect to IFN-γ are particularly important. In both humans and animals, IFN-γ production is associated with the ability to successfully recover from infection with viruses and other pathogens. In addition, it appears that R(−)DMS and S(+)DMS will have a therapeutically beneficial effect for diseases and conditions mediated by weakened host immunity. This would include AIDS, response to vaccines, infectious diseases and adverse immunological effects caused by cancer chemotherapy.

Example 12

Examples of Dosage Forms

A. Desmethylselegiline Patch.

| Dry Weight Basis Component | (mg/cm$^2$) |
|---|---|
| Durotak ® 87-2194 adhesive acrylic polymer | 90 parts by weight |
| Desmethylselegiline | 10 parts by weight |

The two ingredients are thoroughly mixed, cast on a film backing sheet (e.g., Scotchpak® 9723 polyester) and dried. The backing sheet is cut into patches a fluoropolymer release liner (e.g., Scotchpak® 1022) is applied, and the patch is hermetically sealed in a foil pouch. One patch is applied daily to supply 1–10 mg of desmethylselegiline per 24 hours in the treatment of conditions in a human produced by neuronal degeneration or neuronal trauma.

B. Ophthalmic Solution

Desmethylselegiline (0.1 g) as the hydrochloride, 1.9 g of boric acid, and 0.004 g of phenyl mercuric nitrate are dissolved in sterile water qs 100 ml. The mixture is sterilized and sealed. It can be used ophthalmologically in the treatment of conditions produced by neuronal degeneration or neuronal trauma, as for example glaucomatous optic neuropathy and macular degeneration.

C. Intravenous Solution.

A 1% solution is prepared by dissolving 1 g of desmethylselegiline as the HCl in sufficient 0.9% isotonic saline solution to provide a final volume of 100 ml. The solution is buffered to pH 4 with citric acid, sealed, and sterilized to provide a 1% solution suitable for intravenous administration in the treatment of conditions produced by neuronal degeneration or neuronal trauma.

D. Oral Dosage Form

Tablets and capsules containing desmethylselegiline are prepared from the following ingredients (mg/unit dose):

| desmethylselegiline | 1–5 |
|---|---|
| microcrystalline cellulose | 86 |
| lactose | 41.6 |
| citric acid | 0.5–2 |
| sodium citrate | 0.1–2 |
| magnesium stearate | 0.4 | with an approximately 1:1 ratio of citric acid and sodium citrate.

Having now fully described the invention, it will be understood by those of skill in the art that the invention may be performed within a wide and equivalent range of conditions, parameters and the like, without effecting the spirit or scope of the invention or any embodiment thereof.

What is claimed is:

1. A method of treating a condition in a mammal produced by immune system dysfunction that is associated with reduced levels of γ-interferon production, which comprises administering to the mammal the S(+) enantiomer of desmethylselegiline, or a pharmaceutically acceptable acid addition salt thereof at a daily dose, administered in a single or multiple dosage regimen, of at least about 0.015 mg, calculated on the basis of the free secondary amine, per kg of the mammal's body weight, wherein the administration of the S(+) enantiomer of desmethylselegiline or a pharmaceutically acceptable acid addition salt thereof leads to an increase in γ-interferon production in the mammal.

2. The method of claim 1, wherein said S(+) enantiomer of desmethylselegiline is in substantially isomerically pure form.

3. The method of claim 1, wherein the S(+) enantiomer of desmethylselegiline or a pharmaceutically acceptable acid addition salt thereof is administered orally.

4. The method of claim 1, wherein the S(+) enantiomer of desmethylselegiline or a pharmaceutically acceptable acid addition salt thereof is administered non-orally.

5. The method of claim 1, wherein the S(+) enantiomer of desmethylselegiline or a pharmaceutically acceptable acid addition salt thereof is administered parenterally.

6. The method of claim 1, wherein the S(+) enantiomer of desmethylselegiline or a pharmaceutically acceptable acid addition salt thereof is administered transdermally.

7. The method of claim 1, wherein the S(+) enantiomer of desmethylselegiline or a pharmaceutically acceptable acid addition salt thereof is administered either buccally or sublingually.

8. The method of claim 1, wherein the S(+) enantiomer of desmethylselegiline or a pharmaceutically acceptable acid addition salt thereof is administered intravenously.

9. The method of claim 1, wherein the S(+) enantiomer of desmethylselegiline or a pharmaceutically acceptable acid addition salt thereof is administered subcutaneously.

10. The method of claim 1, wherein the S(+) enantiomer of desmethylselegiline or a pharmaceutically acceptable acid addition salt thereof is administered intra-peritoneally.

11. The method of claim wherein the immune system dysfunction is age-dependent.

12. The method of claim 1, wherein the condition produced by immune system dysfunction is AIDS.

13. The method of claim 1, wherein the condition produced by immune system dysfunction is cancer.

14. The method of claim 1, wherein the condition produced by immune system dysfunction is response to a vaccine.

15. The method of claim 1, wherein the daily dose is between about 0.10 mg/kg and about 1.0 mg/kg.

16. The method of claim 1, wherein the daily dose is at least about 1.0 mg/kg.

17. The method of claim 1, wherein the mammal is a human.

18. A method of treating a condition in a mammal produced by immune system dysfunction caused by cancer chemotherapy which is associated with reduced levels of γ-interferon production, which comprises administering to the mammal the S(+) enantiomer of desmethylselegiline, or a pharmaceutically acceptable acid addition salt thereof, at a daily dose, administered in a single or multiple dosage regimen, of at least about 0.015 mg, calculated on the basis of the free secondary amine, per kg of the mammal's body weight, wherein the administration of the S(+) enantiomer of desmethylselegiline or a pharmaceutically acceptable acid addition salt thereof leads to an increase in γ-interferon production in the mammal.

19. The method of claim 18, wherein the S(+) enantiomer of desmethylselegiline is in a substantially isomerically pure form.

20. The method of claim 18, wherein the mammal is a human.

21. A method of treating a condition in a mammal produced by immune system dysfunction that is associated with reduced levels of γ-interferon production, which comprises administering to the mammal the S(+) enantiomer of desmethylselegiline, or a pharmaceutically arable acid addition salt thereof, wherein the administration of the S(+) enantiomer of desmethylselegiline or a pharmaceutically acceptable acid addition salt thereof leads to an increase in γ-interferon production in the mammal.

22. The method of claim 21, wherein the condition produced by immune system dysfunction is caused by infectious disease.

23. The method of claim 21, wherein the S(+) enantiomer of desmethylselegiline is administered at a daily dose of at least about 0.015 mg/kg of the mammal's body weight, calculated on the basis of the free secondary amine.

24. The method of claim 1, wherein the S(+) enantiomer of desmethylselegiline is in a substantially isomerically pure form.

25. The method of claim 1, wherein the mammal is a human.

26. The method of claim 21, wherein the immune system dysfunction is age-dependent.

27. The method of claim 21, wherein the condition produced by immune system dysfunction is AIDS.

28. The method of claim 21, wherein the condition produced by immune system dysfunction is cancer.

29. The method of claim 21, wherein the condition produce by immune system dysfunction is in response to a vaccine.

* * * * *